United States Patent
Briard et al.

(10) Patent No.: US 9,334,271 B2
(45) Date of Patent: May 10, 2016

(54) PURINE DERIVATIVES AND THEIR USE IN THE TREATMENT OF DISEASE

(71) Applicants: Emmanuelle Briard, Huningue (FR); Pascal Furet, Thann (FR); Andreas Lerchner, Binningen (CH); Peter Meier, Allschwil (CH); Branko Radetich, Boston, MA (US); David Andrew Sandham, Horsham (GB); Yanyi Zhu, Acton, MA (US)

(72) Inventors: Emmanuelle Briard, Huningue (FR); Pascal Furet, Thann (FR); Andreas Lerchner, Binningen (CH); Peter Meier, Allschwil (CH); Branko Radetich, Boston, MA (US); David Andrew Sandham, Horsham (GB); Yanyi Zhu, Acton, MA (US)

(73) Assignee: Novarits AG, Basel (CH)

( * ) Notice: Subject to any disclaimer, the term of this patent is extended or adjusted under 35 U.S.C. 154(b) by 0 days.

(21) Appl. No.: 14/353,950

(22) PCT Filed: Oct. 26, 2012

(86) PCT No.: PCT/IB2012/055929
§ 371 (c)(1),
(2) Date: Apr. 24, 2014

(87) PCT Pub. No.: WO2013/061305
PCT Pub. Date: May 2, 2013

(65) Prior Publication Data
US 2014/0336166 A1    Nov. 13, 2014

Related U.S. Application Data

(60) Provisional application No. 61/552,746, filed on Oct. 28, 2012.

(51) Int. Cl.
| | |
|---|---|
| C07D 487/04 | (2006.01) |
| C07D 473/16 | (2006.01) |
| C07D 519/00 | (2006.01) |
| A61K 31/5377 | (2006.01) |
| A61K 31/553 | (2006.01) |
| C07D 491/048 | (2006.01) |
| C07D 491/107 | (2006.01) |

(52) U.S. Cl.
CPC .......... *C07D 473/16* (2013.01); *A61K 31/5377* (2013.01); *A61K 31/553* (2013.01); *C07D 487/04* (2013.01); *C07D 491/048* (2013.01); *C07D 491/107* (2013.01); *C07D 519/00* (2013.01)

(58) Field of Classification Search
CPC .................................................... C07D 487/04
See application file for complete search history.

(56) References Cited

U.S. PATENT DOCUMENTS 3,016,378 A    1/1962    Roch

| | | | |
|---|---|---|---|
| 8,987,257 B2 * | 3/2015 | Radetich et al. ........... 514/232.5 |
| 2002/0058671 A1 | 5/2002 | Elliott |
| 2011/0086840 A1 | 4/2011 | Pei et al. |
| 2011/0086841 A1 | 4/2011 | Pei et al. |
| 2012/0220576 A1 | 8/2012 | Radetich et al. |
| 2015/0344479 A1 | 12/2015 | Radetich et al. |

FOREIGN PATENT DOCUMENTS

| | | |
|---|---|---|
| EP | 2336132 A1 | 6/2011 |
| GB | 864145 | 3/1961 |
| WO | 9320078 A1 | 10/1993 |
| WO | 2006128129 A2 | 11/2006 |
| WO | 2006128172 A2 | 11/2006 |
| WO | 2009053716 A1 | 4/2009 |
| WO | 2009100406 A2 | 8/2009 |
| WO | 2009146406 A1 | 12/2009 |
| WO | 2010002954 | 1/2010 |
| WO | 2010056230 | 5/2010 |
| WO | 2010138589 A1 | 12/2010 |
| WO | 2010144494 A2 | 12/2010 |
| WO | 2011025889 A1 | 3/2011 |
| WO | 2011058027 A2 | 5/2011 |
| WO | 2011078795 A1 | 6/2011 |
| WO | 2012104776 A1 | 8/2012 |
| WO | 2013016305 A1 | 5/2013 |

OTHER PUBLICATIONS

Wang et al.; "Direct C-Arylation of Free (NH)-Indoles and Pyrroles Catalyzed by Ar-Rh(III) Complexes Assembled In Situ"; J. Am. Chem. Soc.; 127:4996-4997 (2005).
Zhao et al.; "Palladium-Catalyzed Direct C-2 Arylation of Indoles with Potassium Aryltrifluoroborate Salts"; J. Org. Chem.; 73:7428-7431 (2008).
International Search Report for International Application No. PCT/IB2012/055929 mailed Jan. 31, 2013. 3 pages.
Brill, Wolfgang K.-D. et al. "Solid-phase Synthesis of 2,6,8-trisubstituted purines." Tetrahedron Letters. Pergamon. Elsevier Science Ltd. vol. 42. Jul. 19, 2001. 4 pages.

* cited by examiner

*Primary Examiner* — Rebecca Anderson
(74) *Attorney, Agent, or Firm* — Shawn D. Britt

(57) ABSTRACT

The invention relates to PI3K inhibitors of the formula (I)• in which all of the variables are as defined in the specification, to their preparation, to their medical use, in particular to their use in the treatment of cancer and neurodegenerative disorders, and to medicaments comprising them.

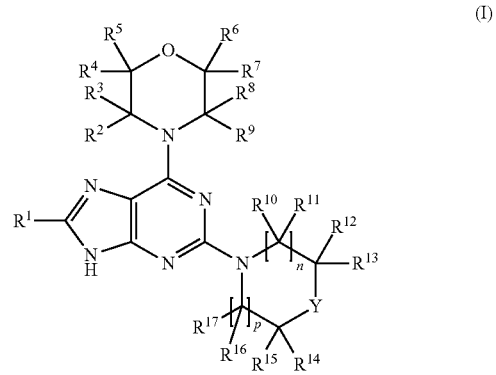

15 Claims, No Drawings

PURINE DERIVATIVES AND THEIR USE IN THE TREATMENT OF DISEASE

CROSS-REFERENCE TO RELATED APPLICATIONS

This application is a U.S. National Phase filing of International Application No. PCT/IB2012/055929 filed Oct. 26, 2012, which claims priority to U.S. Application No. 61/552,746 filed Oct. 28, 2011.

FIELD OF THE INVENTION

The invention relates to purine derivatives and pharmaceutically acceptable salts thereof, processes for their preparation, their use in the treatment of diseases, their use, either alone or in combination with at least one additional therapeutic agent and optionally in combination with a pharmaceutically acceptable carrier, for the manufacture of pharmaceutical preparations, use of the pharmaceutical preparations for the treatment of diseases, and a method of treatment of said diseases, comprising administering the purine derivatives to a warm-blooded animal, especially a human.

BACKGROUND OF THE INVENTION

The phosphatidylinositol-3-kinases superfamily comprises 4 different PI3K related lipid or protein kinases. Class I, II and III are lipid kinases that differ by virtue of their substrate specificities whereas class IV PI3Ks (also called PIKKs) are protein kinases. Class I phosphatidylinositol-3-kinases comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem* 70:535 (2001); Katso et al., *Annu. Rev. Cell Dev. Biol.* 17:615 (2001)). Of the two Class I PI3Ks, Class IA PI3Ks are heterodimers composed of a catalytic p110 subunit (αβ, δ, isoforms) constitutively associated with a regulatory subunit that can be p85α, p55α, p50α, p85β or p55γ. The Class IB sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class IA PI3Ks. Class IB PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class 1 PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, $PIP_2$ and $PIP_3$ recruit Akt, the product of the human homologue of the viral oncogene v-Akt, to the plasma membrane where it acts as a nodal point for many intracellular signaling pathways important for growth and survival (Fantl et al., *Cell* 69:413-423(1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110a isoform, PIK3CA, and for Aid are amplified and increased protein expression of their gene products has been demonstrated in several human cancers. Furthermore, mutations and translocation of p85a that serve to up-regulate the p85-p110 complex have been described in human cancers. Also, somatic missense mutations in PIK3CA that activate downstream signaling pathways have been described at significant frequencies in a wide diversity of human cancers (Kang et al., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey et al., *Nature Rev. Drug Disc.* 4:988-1004 (2005)).

The mammalian target of rapamycin (mTOR) is a member of the class IV PI3K. mTOR assembles a signaling network that transduces nutrient signals and various other stimuli to regulate a wide range of cellular functions including cell growth, proliferation, survival, autophagy, various types of differentiation and metabolism. In mammalian cells, the mTOR protein is found complexed in two distinct entities called mTORC1 and mTORC2. The mTORC1 complex, that is to say mTOR associated with raptor, has been the matter of numerous studies. It is mTORC1 that integrates nutrient and growth factor inputs, and is in turn responsible for cell growth regulation, mainly through protein synthesis regulators such as 4EBP1 or RPS6. mTORC1 regulation requires PI3K and Akt activation for activation, meaning that mTORC1 is an effector of the PI3K pathway. mTOR when associated in the mTOR complex 2 (mTORC2) has been shown to be responsible for the activation of Akt by phosphorylation of S473 (Akt 1 numbering) (Sarbassov et al., *Science* 307:7098 (2005)). mTORC2 is hence here considered as an upstream activator of Akt. Interestingly mTOR can therefore be considered as being important both upstream and downstream of Akt. mTOR catalytic inhibiton might therefore represent a unique way of addressing a very strong block in the PI3K-Akt pathway, by addressing both upstream and downstream effectors.

A link between mTOR inhibition and autophagy has also been demonstrated (Ravikumar et al., *Nat Genet.* 36(6):585-95 (2004)). Autophagy is essential for neuronal homeostasis and its dysfunction has been linked to neurodegeneration. Loss of autophagy in neurons causes neurodegenerative disease in mice (Komatsu et al., *Nature* 441:880-4 (2006); Hara et al., *Nature* 441:885-9 (2006)) suggesting a critical role for autophagy to maintain protein homeostasis in neurons. Neurodegenerative diseases are characterized by inclusions of misfolded proteins as one of the hallmarks. Induction of autophagy enhances clearance of misfolded proteins and thus is proposed as therapy for neurodegenerative proteinopathies.

Huntington's Disease (HD) is an autosomal dominant neurodegenerative disorder where a mutation of IT15 gene encoding the Huntingtin (Htt) protein leads to Polyglutamine expansion in Exon1 of Htt. Intracellular aggregation of this mutant Htt protein and brain atrophy (in particular cortex and striatum) are the main hallmarks of HD. It clinically leads to movement disturbance and cognitive dysfunction besides psychiatric disturbances and weight loss.

Inhibition of mTOR induces autophagy and reduces mutant Htt aggregation and mutant Htt-mediated cell death in in vitro and in vivo models of HD (Ravikumar et al., *Nat Genet.* 36(6):585-95 (2004)). mTOR inhibition therefore provides an opportunity for pharmaceutical intervention and modulation of the disrupted cellular processes characteristic of HD.

In view of the above, mTOR inhibitors are considered to be of value in the treatment of proliferative diseases, such as cancer, and other disorders, in particular, HD.

The present invention relates to novel purine derivatives having mTOR inhibitory activity, their preparation, medical use and to medicaments comprising them.

SUMMARY OF THE INVENTION

In a first aspect, the invention relates to a compound of formula (I), or a pharmaceutically acceptable salt thereof, wherein
$R^1$ is selected from the group consisting of wherein
$R^{18}$ on each occurrence independently represents fluoro or methyl;
m represents 0, 1, 2 or 3;

$R^{19}$ and $R^{20}$ independently represent hydrogen or fluoro;
$R^{21}$ represents fluoro;
$R^{22}$ on each occurrence independently represents fluoro, methoxy, hydroxymethyl or methoxycarbonyl;
q represents 0, 1 or 2 and r represents 0, 1, 2 or 3 provided that q+r is not 0;
$R^2$, $R^3$, $R^4$, $R^5$, $R^6$, $R^7$, $R^8$ and $R^9$ independently represent hydrogen, $C_{1-3}$alkyl or fluoro-$C_{1-3}$alkyl; or $R^3$ and $R^6$ together form a methylene bridge; or $R^3$ and $R^8$ together form an ethylene bridge; or $R^5$ and $R^6$ together form an ethylene bridge;
n and p independently represent 0, 1 or 2;
$R^{10}$, $R^{11}$, $R^{12}$, $R^{13}$, $R^{14}$, $R^{15}$, $R^{16}$ and $R^{17}$ on each occurrence independently represent hydrogen, $C_{1-3}$alkyl, fluoro-$C_{1-3}$alkyl or hydroxy-$C_{1-3}$alkyl; or $R^{11}$ and $R^{16}$ together form an ethylene bridge; or $R^{13}$ and $R^{14}$ together form an ethylene bridge; or $R^{14}$ and $R^{15}$, together with the carbon atom to which they are attached, are linked to form a tetrahydropyranyl ring; and
Y represents O, CHR$^{23}$, CR$^{24}$R$^{25}$ or NR$^{26}$,
wherein
$R^{23}$ represents hydroxyl or fluoro-$C_{1-3}$alkyl; or $R^{23}$ and $R^{13}$, together with the carbon atoms to which they are attached, are linked to form a fused tetrahydrofuranyl ring;
$R^{24}$ and $R^{25}$ independently represent hydrogen or halogen; or $R^{24}$ and $R^{25}$, together with the carbon atom to which they are attached, are linked to form a tetrahydropyranyl ring; and
$R^{26}$ represents $C_{1-3}$alkyl or oxetanyl;
and
a compound, or a pharmaceutically acceptable salt thereof, selected from the following list of compounds:
8-(1H-Indol-4-yl)-6-(3-methyl-morpholin-4-yl)-2-[1,4]oxazepan-4-yl-9H-purine;
8-(1H-Indol-4-yl)-6-(3-methyl-morpholin-4-yl)-2-(3-propyl-morpholin-4-yl)-9H-purine;
8-[8-(1H-Indol-4-yl)-6-(3-methyl-morpholin-4-yl)-9H-purin-2-yl]-8-aza-bicyclo[3.2.1]octan-3-ol;
8-[8-(1H-Indol-4-yl)-6-(3-methyl-morpholin-4-yl)-9H-purin-2-yl]-8-aza-bicyclo[3.2.1]octan-3-ol;
2-(3-Ethyl-morpholin-4-yl)-8-(1H-indol-4-yl)-6-(3-methyl-morpholin-4-yl)-9H-purine;
8-(1H-Indol-4-yl)-6-(3-methyl-morpholin-4-yl)-2-(4-methyl-piperazin-1-yl)-9H-purine;
8-(1H-Indol-4-yl)-6-(3-methyl-morpholin-4-yl)-2-(6-oxa-2-aza-spiro[3.5]non-2-yl)-9H-purine;
8-(1H-Indol-4-yl)-6-(3-methyl-morpholin-4-yl)-2-(4-oxetan-3-yl-piperazin-1-yl)-9H-purine;
8-(1H-Indol-4-yl)-6-(3-methyl-morpholin-4-yl)-2-(tetrahydro-furo[3,4-c]pyrrol-5-yl)-9H-purine;
2-(Hexahydro-furo[3,4-c]pyridin-5-yl)-8-(1H-indol-4-yl)-6-(3-methyl-morpholin-4-yl)-9H-purine;
8-(1H-Indol-4-yl)-2-(3-isopropyl-morpholin-4-yl)-6-(3-methyl-morpholin-4-yl)-9H-purine;
8-(1H-Indol-4-yl)-6-(3-methyl-morpholin-4-yl)-2-(4-trifluoromethyl-piperidin-1-yl)-9H-purine;
2-(2,6-Dimethyl-morpholin-4-yl)-8-(1H-indol-4-yl)-6-(3-methyl-morpholin-4-yl)-9H-purine;
8-(1H-Indol-4-yl)-6-(3-methyl-morpholin-4-yl)-2-(7-oxa-1-aza-spiro[3.5]non-1-yl)-9H-purine;
{4-[8-(1H-Indol-4-yl)-6-(3-methyl-morpholin-4-yl)-9H-purin-2-yl]-morpholin-2-yl}-methanol; and
{4-[8-(1H-Indol-4-yl)-6-(3-methyl-morpholin-4-yl)-9H-purin-2-yl]-morpholin-2-yl}-methanol.

DEFINITIONS

As used herein, the term "halogen" or "halo" refers to fluoro, chloro, bromo, and iodo.

As used herein, the term "$C_{1-3}$alkyl" refers to a fully saturated branched or unbranched hydrocarbon moiety having up to 3 carbon atoms. Representative examples of $C_{1-3}$alkyl include methyl, ethyl, n-propyl and iso-propyl.

As used herein, the term "hydroxy-$C_{1-3}$alkyl" refers to a $C_{1-3}$alkyl group as defined herein above, substituted by one hydroxy radical. Representative examples of hydroxy-$C_{1-3}$alkyl include, but are not limited to, hydroxyl-methyl, 2-hydroxy-ethyl, 2-hydroxy-propyl and 3-hydroxy-propyl.

As used herein, the term "fluoro-$C_{1-3}$alkyl" refers to a $C_{1-3}$alkyl radical, as defined above, substituted by one or more fluoro radicals. Examples of fluoro-$C_{1-3}$alkyl include trifluoromethyl, difluoromethyl, fluoromethyl, 2,2,2-trifluoroethyl, 1-fluoromethyl-2-fluoroethyl and 3,3-difluoropropyl.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

The term "compounds of the present invention" (unless specifically identified otherwise) refer to compounds of formula (I), compounds of the Examples, pharmaceutically acceptable salts of such compounds, and/or hydrates or solvates of such compounds, as well as, all stereoisomers (including diastereoisomers and enantiomers), tautomers and isotopically labeled compounds (including deuterium). The term "agents of the invention" is intended to have the same meaning as "compounds of the present invention".

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "prevention" of any particular disease or disorder refers to the administration of a compound of the invention to a subject before any symptoms of that disease or disorder are apparent.

As used herein, the terms "salt" or "salts" refers to an acid addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, a subject is "in need of" a treatment if such subject would benefit biologically, medically or in quality of life from such treatment.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by mTOR or (ii) associated with mTOR activity, or (iii) characterized by activity (normal or abnormal) of mTOR; (2) reducing or inhibiting the activity of mTOR. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of mTOR. The meaning of the term "a therapeutically effective amount" as illustrated in the above embodiments for mTOR also applies by the same means to any other relevant proteins/peptides/enzymes, such as class IV PI3Ks.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to modulating the disease or disorder, either physically, (e.g., stabilization of a discernible symptom), physiologically, (e.g., stabilization of a physical parameter), or both.

DETAILED DESCRIPTION OF THE INVENTION

The present invention provides compounds and pharmaceutical formulations thereof that may be useful in the treatment or prevention of diseases, conditions and/or disorders modulated by the inhibition of mTOR.

Embodiment 1 a compound of formula (I), or a pharmaceutically acceptable salt thereof, as described hereinbefore.

Embodiment 2 a compound of formula (I), or a pharmaceutically acceptable salt thereof,

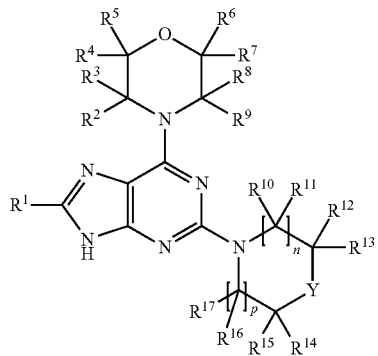

(I)

wherein
$R^1$ is selected from the group consisting of

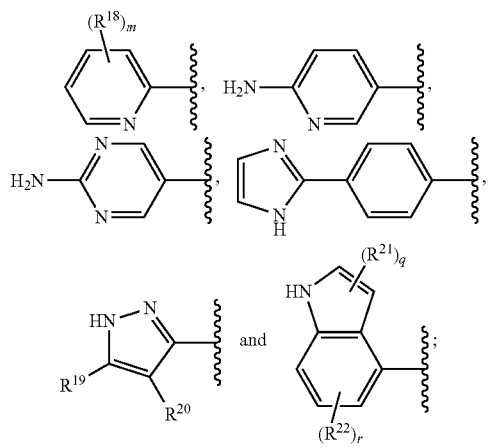

wherein
$R^{18}$ on each occurrence independently represents fluoro or methyl;
m represents 0, 1, 2 or 3;
$R^{19}$ and $R^{29}$ independently represent hydrogen or fluoro;
$R^{21}$ represents fluoro;
$R^{22}$ on each occurrence independently represents fluoro, methoxy, hydroxymethyl or methoxycarbonyl;

q represents 0, 1 or 2 and r represents 0, 1, 2 or 3 provided that q+r is not 0;
$R^2$, $R^3$, $R^4$, $R^5$, $R^6$, $R^7$, $R^8$ and $R^9$ independently represent hydrogen, $C_{1-3}$alkyl or fluoro-$C_{1-3}$alkyl; or $R^3$ and $R^6$ together form a methylene bridge; or $R^3$ and $R^8$ together form an ethylene bridge; or $R^5$ and $R^6$ together form an ethylene bridge;
n and p independently represent 0, 1 or 2;
$R^{10}$, $R^{11}$, $R^{12}$, $R^{13}$, $R^{14}$, $R^{15}$, $R^{16}$ and $R^{17}$ on each occurrence independently represent hydrogen, $C_{1-3}$alkyl, fluoro-$C_{1-3}$alkyl or hydroxy-$C_{1-3}$alkyl; or $R^{11}$ and $R^{16}$ together form an ethylene bridge; or $R^{13}$ and $R^{14}$ together form an ethylene bridge; or $R^{14}$ and $R^{15}$, together with the carbon atom to which they are attached, are linked to form a tetrahydropyranyl ring; and
Y represents O, $CHR^{23}$, $CR^{24}R^{25}$ or $NR^{26}$,
wherein
$R^{23}$ represents hydroxyl or fluoro-$C_{1-3}$alkyl; or $R^{23}$ and $R^{13}$, together with the carbon atoms to which they are attached, are linked to form a fused tetrahydrofuranyl ring;
$R^{24}$ and $R^{25}$ independently represent hydrogen or halogen; or $R^{24}$ and $R^{25}$, together with the carbon atom to which they are attached, are linked to form a tetrahydropyranyl ring; and
$R^{26}$ represents $C_{1-3}$alkyl or oxetanyl.

Embodiment 3 a compound according to Embodiment 1 or Embodiment 2, or a pharmaceutically acceptable salt thereof, wherein $R^1$ represents

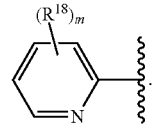

Embodiment 4 a compound according to Embodiment 3, or a pharmaceutically acceptable salt thereof, wherein m represents 0.

Embodiment 5 a compound according to Embodiment 1 or Embodiment 2, or a pharmaceutically acceptable salt thereof, wherein $R^1$ represents

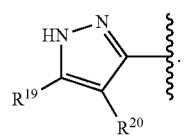

Embodiment 6 a compound according to Embodiment 5, or a pharmaceutically acceptable salt thereof, wherein $R^{19}$ and $R^{20}$ both represent hydrogen.

Embodiment 7 a compound according to Embodiment 1 or Embodiment 2, or a pharmaceutically acceptable salt thereof, wherein $R^1$ represents

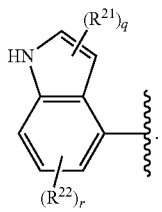

Embodiment 8 a compound according to Embodiment 7, or a pharmaceutically acceptable salt thereof, wherein q represents 0 or 1 and r represents 0, 1 or 2.

Embodiment 9 a compound according to any one of Embodiments 1 to 8, or a pharmaceutically acceptable salt thereof, wherein $R^2$, $R^3$, $R^4$, $R^5$, $R^6$, $R^7$, $R^8$ and $R^9$ independently represent hydrogen or methyl; or $R^3$ and $R^6$ together form a methylene bridge; or $R^3$ and $R^8$ together form an ethylene bridge; or $R^5$ and $R^6$ together form an ethylene bridge.

Embodiment 10 a compound according to any one of Embodiments 1 to 9, or a pharmaceutically acceptable salt thereof, wherein Y represents O.

Embodiment 11 a compound according to any one of Embodiments 1 to 9, or a pharmaceutically acceptable salt thereof, wherein Y represents $CHR^{23}$ or $CR^{24}R^{25}$.

Embodiment 12 a compound, or a pharmaceutically acceptable salt thereof, according to Embodiment 1 which is selected from:
2,6-Bis-(3-methyl-morpholin-4-yl)-8-pyridin-2-yl-9H-purine;
2-(3-Methyl-morpholin-4-yl)-6-(3-methyl-morpholin-4-yl)-8-(1H-pyrazol-3-yl)-9H-purine;
8-(1H-Indol-4-yl)-6-(3-methyl-morpholin-4-yl)-2-[1,4]oxazepan-4-yl-9H-purine;
8-[4-(1H-Imidazol-2-yl)-phenyl]-2,6-bis-(3-methyl-morpholin-4-yl)-9H-purine;
8-(6-Fluoro-1H-indol-4-yl)-2-(3-methyl-morpholin-4-yl)-6-(3-methyl-morpholin-4-yl)-9H-purine;
{4-[2,6-Bis-(3-methyl-morpholin-4-yl)-9H-purin-8-yl]-1H-indol-6-yl}-methanol;
2-(3-Methyl-morpholin-4-yl)-6-(3-methyl-morpholin-4-yl)-8-pyridin-2-yl-9H-purine;
2,6-Bis-(3-methyl-morpholin-4-yl)-8-pyridin-2-yl-9H-purine;
2,6-Di-morpholin-4-yl-8-pyridin-2-yl-9H-purine;
2,6-Bis-(3-methyl-morpholin-4-yl)-8-(1H-pyrazol-3-yl)-9H-purine;
2,6-Bis-(3-methyl-morpholin-4-yl)-8-(1H-pyrazol-3-yl)-9H-purine;
8-(1H-Indol-4-yl)-6-(3-methyl-morpholin-4-yl)-2-(3-propyl-morpholin-4-yl)-9H-purine;
8-[8-(1H-Indol-4-yl)-6-(3-methyl-morpholin-4-yl)-9H-purin-2-yl]-8-aza-bicyclo[3.2.1]octan-3-ol;
8-[8-(1H-Indol-4-yl)-6-(3-methyl-morpholin-4-yl)-9H-purin-2-yl]-8-aza-bicyclo[3.2.1]octan-3-ol;
2-(3-Ethyl-morpholin-4-yl)-8-(1H-indol-4-yl)-6-(3-methyl-morpholin-4-yl)-9H-purine;
8-(1H-Indol-4-yl)-6-(3-methyl-morpholin-4-yl)-2-(4-methyl-piperazin-1-yl)-9H-purine;
8-(1H-Indol-4-yl)-6-(3-methyl-morpholin-4-yl)-2-(6-oxa-2-aza-spiro[3.5]non-2-yl)-9H-purine;
8-(1H-Indol-4-yl)-6-(3-methyl-morpholin-4-yl)-2-(4-oxetan-3-yl-piperazin-1-yl)-9H-purine;
8-(1H-Indol-4-yl)-6-(3-methyl-morpholin-4-yl)-2-(tetrahydro-furo[3,4-c]pyrrol-5-yl)-9H-purine;
2-(Hexahydro-furo[3,4-c]pyridin-5-yl)-8-(1H-indol-4-yl)-6-(3-methyl-morpholin-4-yl)-9H-purine;
8-(1H-Indol-4-yl)-2-(3-isopropyl-morpholin-4-yl)-6-(3-methyl-morpholin-4-yl)-9H-purine;
8-(1H-Indol-4-yl)-6-(3-methyl-morpholin-4-yl)-2-(4-trifluoromethyl-piperidin-1-yl)-9H-purine;
2-(2,6-Dimethyl-morpholin-4-yl)-8-(1H-indol-4-yl)-6-(3-methyl-morpholin-4-yl)-9H-purine;
8-(1H-Indol-4-yl)-6-(3-methyl-morpholin-4-yl)-2-(7-oxa-1-aza-spiro[3.5]non-1-yl)-9H-purine;
{4-[8-(1H-Indol-4-yl)-6-(3-methyl-morpholin-4-yl)-9H-purin-2-yl]-morpholin-2-yl}-methanol;
{4-[8-(1H-Indol-4-yl)-6-(3-methyl-morpholin-4-yl)-9H-purin-2-yl]-morpholin-2-yl}-methanol;
5-[2,6-Bis-(3-methyl-morpholin-4-yl)-9H-purin-8-yl]-pyridin-2-ylamine;
5-[2,6-Bis-(3-methyl-morpholin-4-yl)-9H-purin-8-yl]-pyridin-2-ylamine;
5-[2,6-Bis-(3-methyl-morpholin-4-yl)-9H-purin-8-yl]-pyrimidin-2-yl-amine;
8-[4-(1H-Imidazol-2-yl)-phenyl]-2,6-bis-(3-methyl-morpholin-4-yl)-9H-purine;
8-(6-Methoxy-1H-indol-4-yl)-2-(3-methyl-morpholin-4-yl)-6-(3-methyl-morpholin-4-yl)-9H-purine;
4-[2,6-Bis-(3-methyl-morpholin-4-yl)-9H-purin-8-yl]-1H-indole-6-carboxylic acid methyl ester;
and pharmaceutically acceptable salts thereof.

Embodiment 12 a compound, or a pharmaceutically acceptable salt thereof, according to Embodiment 1 which is selected from:
2,6-Bis-((R)-3-methyl-morpholin-4-yl)-8-pyridin-2-yl-9H-purine;
2-((S)-3-Methyl-morpholin-4-yl)-6-((R)-3-methyl-morpholin-4-yl)-8-(1H-pyrazol-3-yl)-9H-purine;
8-(1H-Indol-4-yl)-6-((R)-3-methyl-morpholin-4-yl)-2-[1,4]oxazepan-4-yl-9H-purine;
8-[4-(1H-Imidazol-2-yl)-phenyl]-2,6-bis-((R)-3-methyl-morpholin-4-yl)-9H-purine;
8-(6-Fluoro-1H-indol-4-yl)-2-((S)-3-methyl-morpholin-4-yl)-6-((R)-3-methyl-morpholin-4-yl)-9H-purine;
{4-[2,6-Bis-((R)-3-methyl-morpholin-4-yl)-9H-purin-8-yl]-1H-indol-6-yl}-methanol;
2-((S)-3-Methyl-morpholin-4-yl)-6-((R)-3-methyl-morpholin-4-yl)-8-pyridin-2-yl-9H-purine;
2,6-Bis-((S)-3-methyl-morpholin-4-yl)-8-pyridin-2-yl-9H-purine;
2,6-Di-morpholin-4-yl-8-pyridin-2-yl-9H-purine;

2,6-Bis-((S)-3-methyl-morpholin-4-yl)-8-(1H-pyrazol-3-yl)-9H-purine;

2,6-Bis-((R)-3-methyl-morpholin-4-yl)-8-(1H-pyrazol-3-yl)-9H-purine;

8-(1H-Indol-4-yl)-6-((R)-3-methyl-morpholin-4-yl)-2-((R)-3-propyl-morpholin-4-yl)-9H-purine;

8-[8-(1H-Indol-4-yl)-6-((R)-3-methyl-morpholin-4-yl)-9H-purin-2-yl]-8-aza-bicyclo[3.2.1]octan-3-ol;

8-[8-(1H-Indol-4-yl)-6-((R)-3-methyl-morpholin-4-yl)-9H-purin-2-yl]-8-aza-bicyclo[3.2.1]octan-3-ol;

2-((R)-3-Ethyl-morpholin-4-yl)-8-(1H-indol-4-yl)-6-((R)-3-methyl-morpholin-4-yl)-9H-purine;

8-(1H-Indol-4-yl)-6-((R)-3-methyl-morpholin-4-yl)-2-(4-methyl-piperazin-1-yl)-9H-purine;

8-(1H-Indol-4-yl)-6-((R)-3-methyl-morpholin-4-yl)-2-(6-oxa-2-aza-spiro[3.5]non-2-yl)-9H-purine;

8-(1H-Indol-4-yl)-6-((R)-3-methyl-morpholin-4-yl)-2-(4-oxetan-3-yl-piperazin-1-yl)-9H-purine;

8-(1H-Indol-4-yl)-6-((R)-3-methyl-morpholin-4-yl)-2-(tetrahydro-furo[3,4-c]pyrrol-5-yl)-9H-purine;

2-(Hexahydro-furo[3,4-c]pyridin-5-yl)-8-(1H-indol-4-yl)-6-((R)-3-methyl-morpholin-4-yl)-9H-purine;

8-(1H-Indol-4-yl)-2-((R)-3-isopropyl-morpholin-4-yl)-6-((R)-3-methyl-morpholin-4-yl)-9H-purine;

8-(1H-Indol-4-yl)-6-((R)-3-methyl-morpholin-4-yl)-2-(4-trifluoromethyl-piperidin-1-yl)-9H-purine;

2-((2S,6R)-2,6-Dimethyl-morpholin-4-yl)-8-(1H-indol-4-yl)-6-((R)-3-methyl-morpholin-4-yl)-9H-purine;

8-(1H-Indol-4-yl)-6-((R)-3-methyl-morpholin-4-yl)-2-(7-oxa-1-aza-spiro[3.5]non-1-yl)-9H-purine;

{(S)-4-[8-(1H-Indol-4-yl)-6-((R)-3-methyl-morpholin-4-yl)-9H-purin-2-yl]-morpholin-2-yl}-methanol;

{(R)-4-[8-(1H-Indol-4-yl)-6-((R)-3-methyl-morpholin-4-yl)-9H-purin-2-yl]-morpholin-2-yl}-methanol;

5-[2,6-Bis-((S)-3-methyl-morpholin-4-yl)-9H-purin-8-yl]-pyridin-2-ylamine;

5-[2,6-Bis-((R)-3-methyl-morpholin-4-yl)-9H-purin-8-yl]-pyridin-2-ylamine;

5-[2,6-Bis-((R)-3-methyl-morpholin-4-yl) 9H-purin-8-yl]-pyrimidin-2-yl-amine;

8-[4-(1H-Imidazol-2-yl)-phenyl]-2,6-bis-((S)-3-methyl-morpholin-4-yl)-9H-purine;

8-(6-Methoxy-1H-indol-4-yl)-2-((S)-3-methyl-morpholin-4-yl)-6-((R)-3-methyl-morpholin-4-yl)-9H-purine;

4-[2,6-Bis-((R)-3-methyl-morpholin-4-yl)-9H-purin-8-yl]-1H-indole-6-carboxylic acid methyl ester; and pharmaceutically acceptable salts thereof.

On account of one or more than one asymmetrical carbon atom, which may be present in a compound of the formula (I), a corresponding compound of the formula (I) may exist in pure optically active form or in the form of a mixture of optical isomers, e. g. in the form of a racemic mixture. All of such pure optical isomers and all of their mixtures, including the racemic mixtures, are part of the present invention.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. Where a compound comprising one or more chiral centers is drawn herein with the stereochemistry indicated in the drawn structure, then the individual optical isomer is intended. Where a compound comprising one or more chiral centers is drawn herein without the stereochemistry indicated in the drawn structure, then no one specific optical isomer is intended and the drawn chemical structure may represent any optical isomer or mixture of isomers having that structure, for example a racemic or diasteriomeric mixture.

In one embodiment, there is provided a compound of the Examples as an isolated stereoisomer wherein the compound has one stereocenter and the stereoisomer is in the R configuration.

In one embodiment, there is provided a compound of the Examples as an isolated stereoisomer wherein the compound has one stereocenter and the stereoisomer is in the S configuration.

In one embodiment, there is provided a compound of the Examples as an isolated stereoisomer wherein the compound has two stereocenters and the stereoisomer is in the R R configuration.

In one embodiment, there is provided a compound of the Examples as an isolated stereoisomer wherein the compound has two stereocenters and the stereoisomer is in the R S configuration.

In one embodiment, there is provided a compound of the Examples as an isolated stereoisomer wherein the compound has two stereocenters and the stereoisomer is in the S R configuration.

In one embodiment, there is provided a compound of the Examples as an isolated stereoisomer wherein the compound has two stereocenters and the stereoisomer is in the S S configuration.

In one embodiment, there is provided a compound of the Examples, wherein the compound has one or two stereocenters, as a racemic mixture.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The compounds of the present invention may be capable of forming acid salts by virtue of the presence of amino groups or groups similar thereto.

In one embodiment, the invention relates to a compound of the formula (I) as defined herein, in free form. In another embodiment, the invention relates to a compound of the formula (I) as defined herein, in salt form. In another embodiment, the invention relates to a compound of the formula (I) as defined herein, in acid addition salt form. In a further embodiment, the invention relates to a compound of the formula (I) as defined herein, in pharmaceutically acceptable salt form. In yet a further embodiment, the invention relates to a compound of the formula (I) as defined herein, in pharmaceutically acceptable acid addition salt form. In yet a further embodiment, the invention relates to any one of the compounds of the Examples in free form. In yet a further embodiment, the invention relates to any one of the compounds of the Examples in salt form. In yet a further embodiment, the invention relates to any one of the compounds of the Examples in acid addition salt form. In yet a further embodiment, the invention relates to any one of the compounds of the Examples in pharmaceutically acceptable salt form. In still another embodiment, the invention relates to any one of the compounds of the Examples in pharmaceutically acceptable acid addition salt form.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts may be derived include, for example, hydrochloric acid, hydrobromic acid, sulfuric acid, nitric acid, phosphoric acid, and the like.

Organic acids from which salts may be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the present invention can be synthesized from an acidic moiety, by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, may also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed.

Suitable co-crystal formers include those described in WO 2004/078163. Hence the invention further provides co-crystals comprising a compound of formula (I).

The compounds of the present invention, including salts, hydrates and solvates thereof, may inherently or by design form polymorphs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

In a further aspect, the invention relates to a process for the preparation of a compound of the formula (I), in free form or in pharmaceutically acceptable salt form, comprising (a) the reaction of a compound of formula (II)

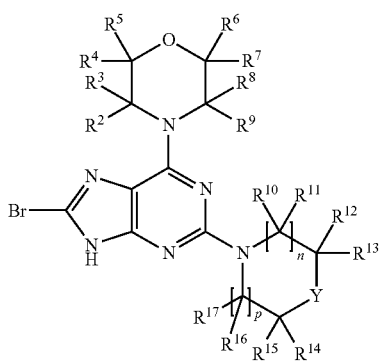

(II)

in which Y, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, n and p are as defined for formula (I), with a compound of formula (III), (IV) or (V)

$$HO\text{-}B(R^1)\text{-}OH$$ (III)

(IV)

(pinacol boronate with $R^1$)

(V)

(tributylstannane with $R^1$)

in which $R^1$ is as defined for formula (I), or (b) the reaction of a compound of formula (VI)

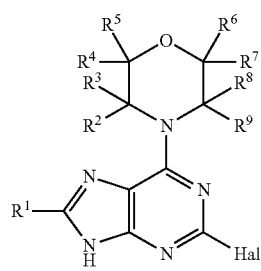

(VI)

in which $R^1$, $R^2$, $R^3$, $R^4$, $R^5$, $R^6$, $R^7$, $R^8$ and $R^9$ are as defined for formula (I) and Hal represents halogen, for example chloro, with a compound of formula (VII)

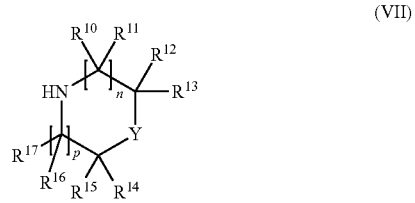

(VII)

in which Y, $R^{10}$, $R^{11}$, $R^{12}$, $R^{13}$, $R^{14}$, $R^{15}$, $R^{16}$, $R^{17}$, n and p are as defined for formula (I), and (c) the optional reduction, oxidation or other functionalisation of the resulting compound, (d) the cleavage of any protecting group(s) present, (e) the recovery of the so obtainable compound of the formula (I) in free form or in pharmaceutically acceptable salt form, (f) the optional separation of mixtures of optically active isomers into their individual optically active isomeric forms.

The reactions can be effected according to conventional methods. For example, the reaction described in step (a) above may be carried out in the presence of a suitable metal catalyst, for example $Pd(PPh_3)_4$ or $PdCl_2(dppf)$, optionally a suitable base, for example cesium fluoride, a suitable solvent, for example toluene or $NEt_3$, acetonitrile/water, and at a suitable temperature, for example 90 to 150° C.

The reaction described in step (b) above may be carried out in the presence of suitable base, for example DIPEA, a suitable solvent, for example 1-butanol, and at a suitable temperature, for example 70 to 90° C.

The further optional reduction, oxidation or other functionalisation of compounds of formula (I) may be carried out according to methods well know to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, and in H.-D. Jakubke and H. Jeschkeit, "Aminosäuren, Peptide, Proteine" (Amino acids, Peptides, Proteins), Verlag Chemie, Weinheim, Deerfield Beach, and Basel 1982. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, acid addition salts of compounds of the present invention are obtained in customary manner, e.g. by treating the compounds with an acid or a suitable anion exchange reagent.

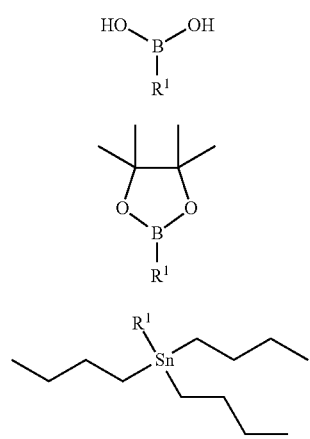

Salts can be converted into the free compounds in accordance with methods known to those skilled in the art. Acid addition salts can be converted, for example, by treatment with a suitable basic agent.

Any resulting mixtures of isomers can be separated on the basis of the physicochemical differences of the constituents, into the pure or substantially pure geometric or optical isomers, diastereomers, racemates, for example, by chromatography and/or fractional crystallization.

For those compounds containing an asymmetric carbon atom, the compounds exist in individual optically active isomeric forms or as mixtures thereof, e.g. as racemic or diastereomeric mixtures. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a commercially available chiral HPLC column.

The invention further includes any variant of the present processes, in which the reaction components are used in the form of their salts or optically pure material. Compounds of the invention and intermediates can also be converted into each other according to methods generally known to those skilled in the art.

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1. General Procedure 1 for synthesis of purine compounds

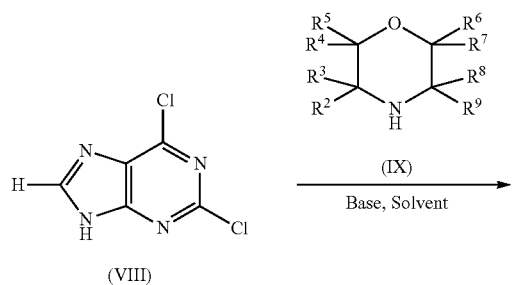

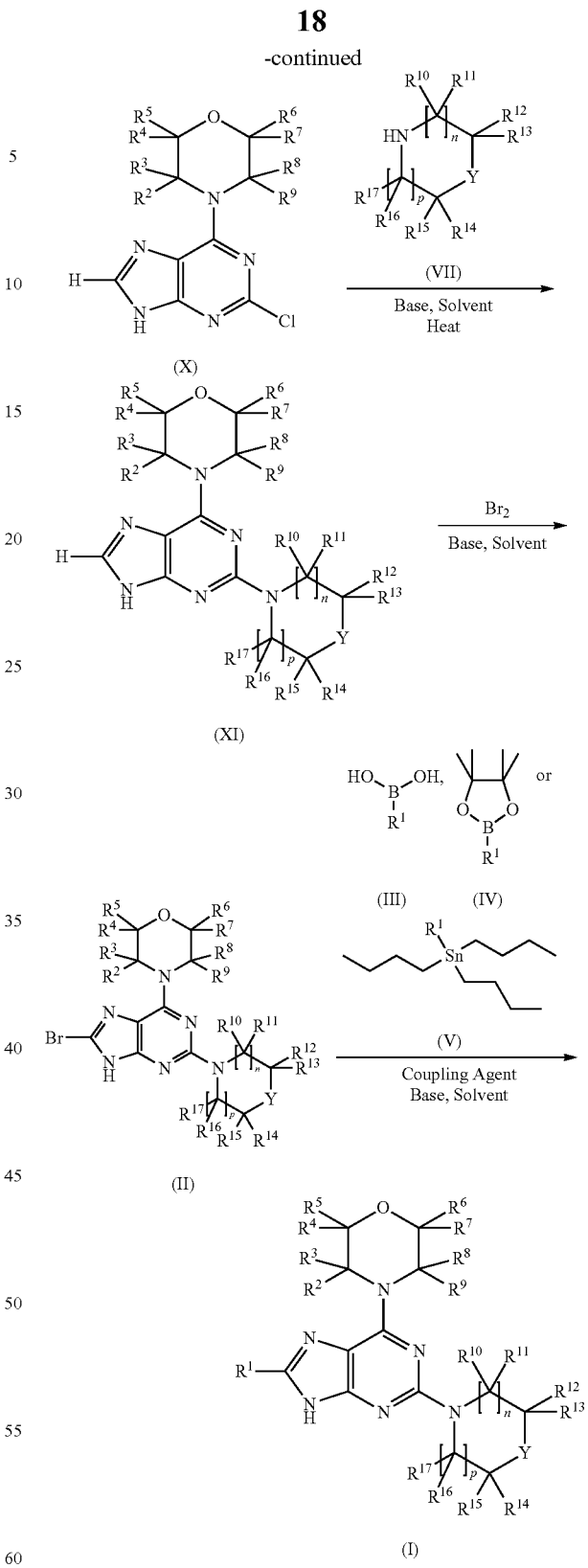

Generally, the compounds of formula (I) can be prepared according to Scheme 1 in four steps, starting from commercially available material (VIII). As to the individual steps in the scheme shown above, step one involves preparation of the intermediate (X) by chlorine displacement with a nucleophile such as functionalized morpholino intermediate (IX). Intermediate (XI) can be prepared by reaction of intermediate (X) with intermediate (VII) in the presence of adequate base such as diisopropylethyl amine, solvent such as dimethyl acetamide and heat. Step three involves bromination of intermediate (XI) to intermediate (II) utilizing bromine in an appropriate solvent such as dichloromethane. Target compounds of formula (I) can be prepared by coupling intermediate (II) with a variety of commercially available or synthesized boronic acids or esters of structures (III) or (IV), or tributylstannyl derivatives of formula (V), using metal catalysts most often exemplified by commercially available palladium complexes.

Scheme 2. General Procedure 2 for synthesis of purine compounds

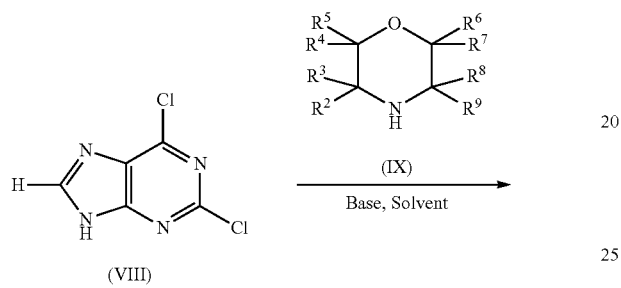

(VIII)

(IX)
Base, Solvent

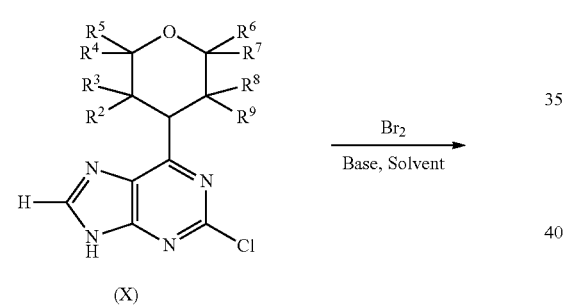

(X)

Br$_2$
Base, Solvent

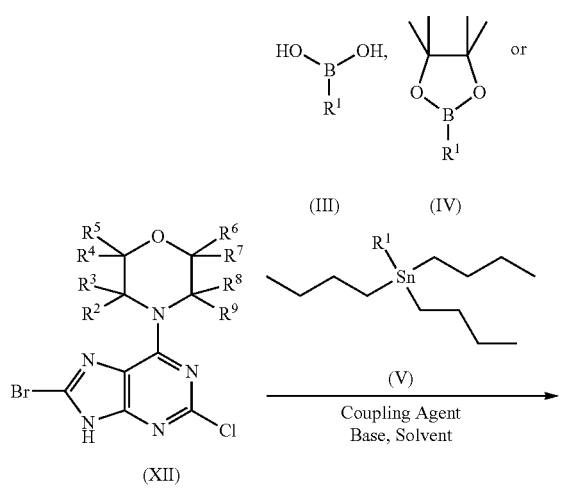

(XII)

(III)    (IV)

(V)
Coupling Agent
Base, Solvent

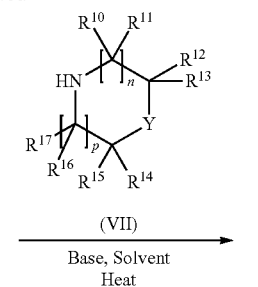

(XIII)

(VII)
Base, Solvent
Heat (I)

Generally, the compounds of formula (I) can be prepared according to Scheme 2 in four steps, starting from commercially available material (VIII). As to the individual steps in the scheme shown above, step one involves preparation of the intermediate (X) by chlorine displacement with a nucleophile such as a functionalized morpholino intermediate of formula (IX). Intermediate (XII) can be prepared by bromination of intermediate (X) in the presence of an appropriate solvent such as dichloromethane. Step three involves the coupling of intermediate (XII) with a variety of commercially available or synthesized boronic acids or esters of structures (III) or (IV), or tributylstannyl derivatives of formula (V), using metal catalysts most often exemplified by commercially available palladium complexes. Target compounds of formula (I) can be prepared by treatment of the intermediate (XIII) with a functionalized morpholino intermediate (VII) in the presence of adequate base such as diisopropylethyl amine, solvent such as dimethyl acetamide and heat or under microwave irradiation.

Scheme 3. General Procedure for synthesis of boronic esters.

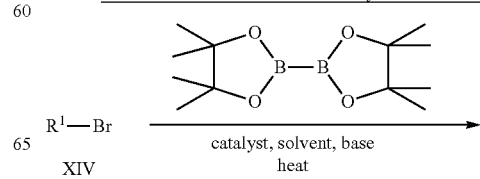

R$^1$—Br    catalyst, solvent, base
XIV          heat

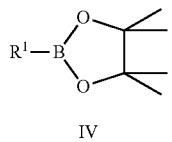

IV

Boronic esters of formula (IV) can be prepared according to Scheme 3 in one step where $R^1$ is as described in formula (I). The step involves reacting substituted arylbromide or heteroarylbromide of formula (XIV) with bis(pinacolato)diboron in the presence of a commercially available palladium catalyst, a solvent such as dioxane, and at a temperature ranging from 80° C. to 120° C.

The invention further includes any variant of the present processes, in which the reaction components are used in the form of their salts or optically pure material. Compounds of the invention and intermediates can also be converted into each other according to methods generally known to those skilled in the art.

Compounds of the formula (I), in free form or in pharmaceutically acceptable salt form, hereinafter often referred to as "agents of the invention", exhibit valuable pharmacological properties, when tested in vitro, and may, therefore, be useful in medicaments, in therapy or for use as research chemicals, for example as tool compounds.

The agents of the invention are inhibitors of mTOR. The inhibiting properties of a compound of the invention towards mTOR can be evaluated in tests as described hereinafter.

Biological Assays

Test 1: mTOR ATP-Binding Assay Based on TR-FRET for Recombinant Human mTOR 1. 8-point serial dilutions of compounds (10 mM stock) are performed in 90% DMSO in a 384-well "masterplate" and 50 nL is transferred onto 384-well assay plates (white polystyrene small volume; Matrix/Thermo Scientific Cat. No. #4365).

2. The final volume of the assay is 10 μL and the order of addition is as follows:

50 nL of compounds dilution;
5 μL of a mixture of GST-mTOR and Europium anti-GST antibody with or without the PI3K/mTOR inhibitor P1-103 (3-(4-(4-morpholinyl)pyrido[3',2':4,5]furo[3,2-d]pyrimidin-2-yl)phenol, Calbiochem);
5 μL of tracer-314.
Incubated for 60 minutes at room temperature.
TR-FRET measured in Biotek Synergy2 reader at:
Excitation 340 nm/emission 665 nm
Excitation 340 nm/emission 620 nm The assay buffer consists of 50 mM HEPES pH 7.5, 5 mM MgCl2, 1 mM EGTA, 0.01% Pluronic F-127. Tracer-314 (Alexa Fluor® 647-labeled ATP-competitive kinase inhibitor; Cat. No. PV6087), Europium anti-GST antibody (Cat. No PV5594) and N-terminally GST-tagged truncated human mTOR (FRAP1) (Cat. No PV4754) are available from Invitrogen.

The following final concentrations are used:
3 nM GST-mTOR;
1 nM Europium anti-GST antibody;
+/−10 μM P1-103; and
10 nM tracer-314.

The final concentrations of diluted compounds are 9091; 2730; 910; 273; 91; 27; 9; and 3 nM. The final concentration of DMSO is 0.45%

The following controls are used:
High signal: solvent vehicle, GST-mTOR, Eu-anti-GST antibody, tracer-314;
Low signal: solvent vehicle, GST-mTOR, Eu-anti-GST antibody, P1-103, tracer-314.

3. $IC_{50}$ determinations may be performed as follows:
Raw signal at 340/665 is divided by the raw signal at 340/620 to give an emission ratio. The Emission ratio is converted to percentage of inhibition for each compound concentration. $IC_{50}$ values are calculated by fitting a sigmoidal dose-response curve to a plot of assay readout over compound concentration. All fits and analysis are performed with the program XLfit4 (ID Business Solutions, Guildford, UK).

Test 2: Cellular mTOR Assay

A cell based assay (384-well format) was developed for determination of compound effects on cellular mTOR kinase activity in MEFs (mouse embryo fibrobrasts) cells derived from mice lacking TSC1 (Tuberosclerosis Complexi) a potent suppressor of mTOR kinase activity. Due to lack of TSC1 the mTOR kinase is constitutively activated resulting in permanently enhanced phosphorylation of Thr 389 of S6 kinase 1 (S6K1) which is one of the downstream targets of mTOR (Kwiatkowski D. J., Zhang H., Bandura J. L. et al. (2002)] A mouse model of TSC1 reveals sex-dependent lethality from liver hemangiomas, and up-regulation of p70S6 kinase activity in TSC null cells. Hum. Mol. Gen. 11: 525-534).

Day 0:
Cell Seeding:
Subconfluent TSC1−/− MEFs are cultured in DMEM High glucose supplemented with 10% Heat Inactivated FCS and 2% Hepes. mTOR is constitutively active in these cells leading to permanently enhanced phosphorylation of p70S6 kinase. The cells are harvested by trypsinization, resuspended in growth medium, counted and adjusted to 133,333 cells/ml. 30 μl are added per well to a 384 well-plate using a Multidrop instrument (Thermo scientific), resulting in 4000 cells/well. The plates are incubated at 37° C./5% $CO_2$ for 20 hours (to allow for settling and adherance to the surface).

Day 1:
Compound Treatment:
Eight 3-fold serial dilutions of test-compounds (beginning at 1.8 mM) are prepared in 90% DMSO and compiled on 384 well master plates (Greiner). A pan-pPI3K/mTOR inhibitor (0.8 mM of 8-(6-methoxy-pyridin-3-yl)-3-methyl-1-(4-piperazin-1-yl-3-trifluoromethyl-phenyl)-1,3-dihydro-imidazo[4,5-c]quinolin-2-one in 90% DMSO) is added to the wells for the low control. 90% DMSO is added to the wells for the high controls. Compounds are provided as 250 nl shots (Hummingbird) in 384 well-polypropylene microplates (compound plates). 50 μl of growth medium is added to the compound plates (dilution 1:200) with the Multidrop. After shaking (1 min at 2000 rpm), 10 μl of the first dilution is then transferred to the cell plate with a Matrix Plate Mate 2×3 pipettor (final dilution 1:4). After 1 hour of treatment, medium is removed from the plate and 20 μl of Surefire lysis buffer is added per well with the Multidrop.

Surefire Assay:
Cell lysates are frozen for 15 minutes, thawed with shaking and transferred to the experimental 384 well-Proxiplate (5 μl/well) for the P-P70S6K (T389) Surefire assay (Perkin Elmer #TGR70S50). The first mix is composed of the reaction buffer (containing the specific antibody), the activation buffer and the acceptor beads (40 vol, 10 vol and 1 vol respectively). 5 μl per well is added to the lysates with a Zephyr® SPE Workstation (Caliper Life Sciences) and incubated for 2 hours with shaking at room temperature. After this incubation time, the second mix of dilution buffer and donor beads (20 vol and 1 vol respectively) is added to the plate with the same instrument (2 µl/well). After 2 hours, the plate can be read with an EnVision® Multilabel Reader (Perkin Elmer). Since the beads are light sensitive, their transfer and incubation is executed in a dark room (greenlight).

Day 2:
Data Analysis:

The raw data is used to generate dose response curves for test compounds and $IC_{50}$ values calculated therefrom.

Test 3: Autophagy Assay

Autophagy is a catabolic pathway that degrades bulk cytosol in lysosomal compartments enabling amino acids and fatty acids to be recycled. One of the key regulators of autophagy is the mammalian target of rapamycin (mTOR), a conserved serine/threonine kinase which suppresses the initiation of the autophagic process when nutrients, growth factors and energy are available. To quantify autophagy induction by mTOR inhibitors, we use a mCherry-GFP-LC3 reporter which is amenable to retroviral delivery into mammalian cells, stable expression and analysis by fluorescence microscopy.

mCherry-GFP-LC3 Reporter

The amino acid sequence of the mCherry-GFP-LC3 construct is shown below (SEQ ID NO: 1). The mCherry sequence is underlined, GFP sequence is in bold and LC3A sequence is boxed.

MVSKGEEDNMAIIKEFMRFKVHMEGSVNGHEFEIEGEGEGRPYEGTQTAK

LKVTKGGPLPFAWDILSPQFMYGSKAYVKHPADIPDYLKLSFPEGFKWER

VMNFEDGGVVTVTQDSSLQDGEFIYKVKLRGTNFPSDGPVMQKKTMGWEA

SSERMYPEDGALKGEIKQRLKLKDGGHYDAEVKTTYKAKKPVQLPGAYNV

NIKLDITSHNEDYTIVEQYERAEGRHSTGGMDELYKPVATMVSKGEELFT

GVVPILVELDGDVNGHKFSVSGEGEGDATYGKLTLKFICTTGKLPVPWPT

LVTTLTYGVQCFSRYPDHMKQHDFFKSAMPEGYVQERTIFFKDDGNYKTR

AEVKFEGDTLVNRIELKGIDFKEDGNILGHKLEYNYNSHNVYIMADKQKN

GIKVNFKIRHNIEDGSVQLADHYQQNTPIGDPVLLPDNHYLSTQSALSK

DPNEKRDHMVLLEFVTAAGITLGMDELYKSGLRSRAGASNSAVD MPSDRP

FKQRRSFADRCKEVQQIRDQHPSKIPVIIERYKGEKQLPVLDKTKFLVPD

HVNMSELVKIIRRRLQLNPTQAFFLLVNQHSMVSVSTPIADIYEQEKDED

GFLYMVYASQETFGF

Described hereinafter is an imaging protocol and image recognition algorithm to visualize and measure changes in the autophagic pathway.

Quantification of Autophagy Using High-Content Imaging and Analysis

1. Day 0: Cell plating. Subconfluent H4 mCherry-GFP-LC3 cells are harvested by trypsinization, resuspended in growth medium, and counted (H4 cells: Human neuroglioma cell line (ATCC)). A cell suspension of 66'000 cells/mL is prepared and 30 µL are added into the wells of a 384-well plate using an electronic multichannel pipette. This results in 2000 cells/well being plated. The cell plates are briefly spun down and placed at 37° C. and 5% $CO_2$.

2. Day 1: Compound treatment. Compound dose responses are prepared in DMSO. The dose responses are then diluted 1:50 in medium. 10 ul of the diluted compound is added to 30 ul of cells, yielding a final 1:200 dilution of the original compound and final of 0.5% DMSO. Compound-treatments are performed in triplicates. The 384-well plates are placed at 37° C. and 5% $CO_2$. Compound treatment is performed for 16-18 h (see Note 1).

3. Day 2: Cell fixation. Cells are fixed by adding 10 µL/well 5× concentrated Mirsky's fixative supplemented with 25 µg/mL Hoechst33342. This results in a total volume of 50 µL per well and a concentration of 1× Mirsky's fixative and 5 µg/mL Hoechst33342. The 384-well plate is briefly spun down and incubated for 1 h at room temperature. Cells are then washed using a 384-well plate washer using a protocol which aspirates the volume down to 10 µL/well before dispensing 100 µL/well 1×TBS. Aspiration and dispensing steps are repeated 4 times and a final volume of 100 µL/well is left. The plate is sealed using an adhesive PCR foil.

4. Imaging. The bottom of the plate is cleaned with 70% ethanol and then imaged using the InCell 1000 automated epifluorescence microscope. 20× magnification is used and 4 different areas (fields) are imaged per well, this typically captures a total of around 400 cells per well. Hoechst33342 images are acquired using an excitation of 360 nm (D360_40x filter), an emission of 460 nM (HQ460_40M filter) and an exposure time of 150 ms. GFP images are acquired using an excitation of 475 nm (S475_20x filter), an emission of 535 nM (HQ535_50M filter) and an exposure time of 1 s. mCherry images are acquired using an excitation of 535 nm (HQ535_50x filter), an emission of 620 nM (HQ620_60M filter) and an exposure time of 1 s. A quadruple band pass mirror is used for all images.

5. Image analysis. The InCell Analysis software is used to analyze the images using the Multi Target Analysis algorithm. First, nuclei are detected in the Hoechst33342 image using top-hat segmentation and a minimal nuclear area of 50 µm². Cells are defined using a collar of 10 µm around the nuclei. Second, puncta (organelles) are identified in the mCherry image inside the cells using multi-top-hat segmentation. Third, the mask of the mCherry puncta is transferred onto the GFP image. Fourth, the GFP fluorescence intensity inside the mCherry puncta mask is measured (reference intensity).

6. The 'organelles' parameter reflects mCherry-positive puncta of the mCherry-GFP-LC3 reporter and is used to calculate 'LC3 puncta/cell'. For this purpose, the number of organelles is calculated per cell and averaged over all the cells in a given well (average per cell basis). mCherry-positive LC3 puncta numbers (y-axis) are plotted against the compound dose response values (x-axis) and EC50 values are calculated for each compound. EC50 values represent compound potency in terms of autophagy activation (e.g. increase in mCherry-positive LC3 puncta count).

Notes

1. Autophagy-modulation and redistribution of mCherry-GFP-LC3 can be already observed after a compound treatment time of 3-4 h. However, more robust effects are seen with 16-18 h treatment times.

The compounds of the Examples showed the values presented in Table 1 below when tested in the above assays.

TABLE 1

| Example Number | Test 1: mTOR binding assay $IC_{50}$ (nM) | Test 2: T389 cellular assay $IC_{50}$ (nM) | Test 3: Autophagy $EC_{50}$ (nM) |
| --- | --- | --- | --- |
| 1 | 139 | 1010 | 351 |
| 2 | 104 | 131 | 1050 |
| 3 | 164 | 76 | 422 |
| 4 | 2122 | 1550 | 2155 |
| 5 | 21 | 122 | n.d. |
| 6 | 66 | 1185 | 423 |
| 7 | 184 | 997 | 1317 |
| 8 | 1027 | 806 | n.m. |
| 9 | 860 | n.d. | n.d. |
| 10 | 343 | 135 | 1439 |
| 11 | 385 | 190 | 1524 |
| 12 | 194 | 534 | 674 |
| 13 | 143 | 618 | 935 |
| 14 | 76 | 250 | 855 |
| 15 | 60 | 194 | 752 |
| 16 | 308 | 259 | n.m. |
| 17 | 112 | 224 | 663 |
| 18 | 91 | 249 | n.m. |
| 19 | 296 | 471 | 727 |
| 20 | 484 | 319 | n.m. |
| 21 | 122 | 179 | n.d. |
| 22 | 1510 | 1040 | 1682 |
| 23 | 78 | 104 | n.m. |
| 24 | 369 | 229 | 302 |
| 25 | 380 | 1930 | n.d. |
| 26 | 67 | 318 | n.d. |
| 27 | 2412 | 1191 | 4743 |
| 28 | 754 | 272 | 2371 |
| 29 | 1314 | 498 | 3606 |
| 30 | 364 | 1137 | 1457 |
| 31 | 28 | 71 | 145 |
| 32 | 533 | 1120 | >6000 | n.d. = not determined;
n.m. = not measurable

As indicated by the test results described hereinbefore, compounds of the present invention may be useful for treating diseases, conditions and disorders modulated by the inhibition of the mTOR enzyme; consequently, the compounds of the present invention (including the compositions and processes used therein) may be used in the manufacture of a medicament for the therapeutic applications described herein. Hence, another embodiment of the present invention is a pharmaceutical composition comprising a compound of the present invention, or a pharmaceutically acceptable salt thereof, and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In one embodiment, the invention relates to the treatment of cellular proliferative diseases such as tumor and/or cancerous cell growth mediated by mTOR. Diseases may include those showing overexpression or amplification of PI3K alpha, Rheb, somatic mutation of PIK3CA or germline mutations or somatic mutation of PTEN, TSC1, TSC2, or mutations and translocation of p85a that serve to up-regulate the p85-p110 complex. In particular, the compounds are useful in the treatment of human or animal (e.g., murine) cancers, including, for example, sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia vera; essential thrombocythemia; myelofibrosis with myeloid metaplasia; and Walden stroem disease.

In other embodiments, the condition or disorder is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

Additional syndromes with an established or potential molecular link to dysregulation of mTOR kinase activity are, for instance, described in "K. Inoki et al.; Disregulation of the TSC-mTOR pathway in human disease, Nature Genetics, vol 37, 19-24"; "D. M. Sabatini; mTOR and cancer: insights into a complex relationship, Nature Reviews, vol. 6, 729-734"; and in "B. T. Hennessy et al.; Exploiting the PI3K/Akt pathway for cancer drug discovery, Nature Reviews, vol. 4, 988-1004", and are as follows:

Organ or tissue transplant rejection, e.g. for the treatment of recipients of e.g. heart, lung, combined heart-lung, liver, kidney, pancreatic, skin or corneal transplants; graft-versus-host disease, such as following bone marrow transplantation;
Restenosis
Tuberous sclerosis
Lymphangioleiomyomatosis
Retinitis pigmentosis and other retinal degenerative disorders
Autoimmune diseases including encephalomyelitis, insulin-dependent diabetes mellitus, lupus, dermatomyositis, arthritis and rheumatic diseases
Steroid-resistant acute Lymphoblastic Leukaemia
Fibrotic diseases including scleroderma, pulmonary fibrosis, renal fibrosis, cystic fibrosis
Pulmonary hypertension
Immunomodulation
Multiple sclerosis
VHL syndrome
Carney complex
Familial adenonamtous polyposis
Juvenile polyposis syndrome
Birt-Hogg-Duke syndrome
Familial hypertrophic cardiomyopathy
Wolf-Parkinson-White syndrome
Neurodegenerative disorders such as Parkinson's Disease, Huntington's Disease, Alzheimer's Disease and dementias caused by tau mutations, spinocerebellar ataxia type 3, motor neuron disease caused by SOD1 mutations, neuronal ceroid lipofucinoses/Batten disease (pediatric neurodegeneration)
Ophthalmological diseases such as wet and dry macular degeneration, uveitis, including autoimmune uveitis, retinopathy, such as diabetic retinopathy or hyperbaric oxygen-induced retinopathy, and glaucoma
muscle wasting (atrophy, cachexia) and myopathies such as Danon's disease.
bacterial and viral infections including *M. tuberculosis*, group A streptococcus, HSV type I, HIV infection
Neurofibromatosis including Neurofibromatosis type 1, and
Peutz-Jeghers syndrome, Cowden's disease.

Compounds with an inhibitory activity on mTORC1 have shown benefit in immunomodulation and in treating proliferative diseases such as advance renal cell carcinoma or Tubero-Sclerosis (TSC) germ line mutation associated disorders.

For the above uses the required dosage will of course vary depending on the mode of administration, the particular condition to be treated and the effect desired. In general, satisfactory results are indicated to be obtained systemically at daily dosages of from about 0.03 to about 100.0 mg/kg per body weight, e.g. about 0.03 to about 10.0 mg/kg per body weight. An indicated daily dosage in the larger mammal, e.g. humans, is in the range from about 0.5 mg to about 3 g, e.g. about 5 mg to about 1.5 g, conveniently administered, for example, in divided doses up to four times a day or in retard form. Suitable unit dosage forms for oral administration comprise from ca. 0.1 to about 500 mg, e.g. about 1.0 to about 500 mg active ingredient.

In general, compounds of the present invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the present invention is inhalation. This is an effective method for delivering a therapeutic agent directly to the respiratory tract.

Consequently, the invention also provides:
a method for preventing or treating conditions, disorders or diseases mediated by the activation of the PI3K (e.g. PI3 kinase alpha) and/or mTOR enzymes e.g. such as indicated above, in a subject in need of such treatment, which method comprises administering to said subject an effective amount of a compound of the present invention or a pharmaceutically acceptable salt thereof. In one embodiment, there is provided a method for preventing or treating cancer, a neurodegenerative disorder or an ophthalmological disease, in a subject in need of such treatment, which method comprises administering to said subject an effective amount of a compound of the present invention or a pharmaceutically acceptable salt thereof. In another embodiment, the neurodegenerative disorder is Parkinson's, Huntington's or Alzheimer's Disease. In yet another embodiment, the neurodegenerative disorder is Huntington's Disease.
a compound of the present invention, or a pharmaceutically acceptable salt thereof, for use as a medicament, e.g. in any of the conditions, disorders or diseases indicated herein, in particular for the use in one or more phosphatidylinositol 3-kinase mediated diseases. In one embodiment, there is provided a compound of the present invention, or a pharmaceutically acceptable salt thereof, for use in the treatment or prevention of cancer, a neurodegenerative disorder or an ophthalmological disease. In another embodiment, the neurodegenerative disorder is Parkinson's, Huntington's or Alzheimer's Disease. In yet another embodiment, the neurodegenerative disorder is Huntington's Disease.

the use of a compound of the present invention, or a pharmaceutically acceptable salt thereof, as an active pharmaceutical ingredient in a medicament, e.g. for the treatment or prevention of any of the conditions, disorders or diseases indicated herein, in particular for the treatment or prevention of one or more phosphatidylinositol 3-kinase mediated diseases. In one embodiment, there is provided the use of a compound of the present invention, or a pharmaceutically acceptable salt thereof, as an active pharmaceutical ingredient in a medicament for the treatment or prevention of cancer, a neurodegenerative disorder or an ophthalmological disease. In another embodiment, the neurodegenerative disorder is Parkinson's, Huntington's or Alzheimer's Disease. In yet another embodiment, the neurodegenerative disorder is Huntington's Disease.

the use of a compound of the present invention, or a pharmaceutically acceptable salt thereof, for the manufacture of a medicament for the treatment or prevention of one or more phosphatidylinositol 3-kinase mediated diseases. In one embodiment, there is provided the use of a compound of the present invention, or a pharmaceutically acceptable salt thereof, for the manufacture of a medicament for the treatment or prevention of cancer, a neurodegenerative disorder or an ophthalmological disease. In another embodiment, the neurodegenerative disorder is Parkinson's, Huntington's or Alzheimer's Disease. In yet another embodiment, the neurodegenerative disorder is Huntington's Disease.

An agent of the invention can be administered as sole active pharmaceutical ingredient or as a combination with at least one other active pharmaceutical ingredient effective, e. g., in the treatment or prevention of cancer or a neurodegenerative disorder. Such a pharmaceutical combination may be in the form of a unit dosage form, which unit dosage form comprises a predetermined quantity of each of the at least two active components in association with at least one pharmaceutically acceptable excipient, diluent or carrier. Alternatively, the pharmaceutical combination may be in the form of a package comprising the at least two active components separately, e. g. a pack or dispenser-device adapted for the concomitant or separate administration of the at least two active components, in which these active components are separately arranged. In a further aspect, the invention relates to such pharmaceutical combinations.

In a further aspect, the invention therefore relates to a combination product comprising an agent of the invention, or a pharmaceutically acceptable salt thereof, and another therapeutic agent.

In one embodiment, the combination product is a pharmaceutical composition comprising an agent of the invention, or a pharmaceutically acceptable salt thereof, and another therapeutic agent, and a pharmaceutically acceptable excipient, diluent or carrier.

In one embodiment, the combination product is a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In view of their mTOR inhibitory activity, compounds of the invention, either alone or combination, may be useful in the treatment of cancer. In one embodiment, the invention therefore relates to a compound of the invention, or a pharmaceutically acceptable salt thereof, in combination with another therapeutic agent wherein the other therapeutic agent is selected from the group of anticancer agents set forth below:

(a) Kinase Inhibitors: for example inhibitors of Epidermal Growth Factor Receptor (EGFR) kinases such as small molecule quinazolines, including gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

(b) Anti-Estrogens: such as Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

(c) Anti-Androgens: such as flutamide, bicalutamide, finasteride, aminoglutethamide, ketoconazole, and corticosteroids.

(d) Other Inhibitors: such as protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; and cyclooxygenase 2 (COX-2) inhibitors including non-steroidal antiinflammatory drugs I (NSAIDs).

(e) Cancer Chemotherapeutic Drugs: such as anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

(f) Alkylating Agents: such as VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

(g) Chelating Agents: such as tetrathiomolybdate (WO 01/60814); RP-697; Chimeric T84.66 (cT84.66); gadofosveset (Vasovist®); deferoxamine; and bleomycin optionally in combination with electorporation (EPT).

(h) Biological Response Modifiers: such as immune modulators, including staurosprine and macrocyclic analogs thereof, including UCN-ol, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexalen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

(i) Cancer Vaccines: including Avicine® (Tetrahedron Lett. 26:2269-70 (1974)); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

(j) Antisense Therapy: including antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

Thus, in another embodiment, the invention provides a pharmaceutical composition comprising;
i) a compound of the invention, or a pharmaceutically acceptable salt thereof, and
ii) at least one compound selected from
    (a) kinase inhibitors,
    (b) anti-estrogens,
    (c) anti-androgens,
    (e) cancer chemotherapeutic drugs,
    (f) alkylating agents,
    (g) chelating agents,
    (h) biological response modifiers, and
ii) one or more pharmaceutically acceptable excipient, diluent or carrier.

In one embodiment, the invention provides a pharmaceutical composition comprising a compound of the invention, or a pharmaceutically acceptable salt thereof, and everolimus (Afinitor®).

In view of their mTOR inhibitory activity, compounds of the invention, either alone or combination, may be useful in the treatment of neurodegenerative disorders. In one embodiment, the invention therefore relates to a compound of the invention, or a pharmaceutically acceptable salt thereof, in combination with another therapeutic agent wherein the other therapeutic agent is selected from:
(a) acetylcholinesterase inhibitors: such as donepezil (Aricept™), rivastigmine (Exelon™) and galantamine (Razadyne™);
(b) glutamate antagonists: such as memantine (Namenda™);
(c) antidepressant medications: for low mood and irritability such as citalopram (Celexa™) fluoxetine (Prozac™), paroxeine (Paxil™), sertraline (Zoloft™) and trazodone (Desyrel™);
(d) anxiolytics: for anxiety, restlessness, verbally disruptive behavior and resistance, such as lorazepam (Ativan™) and oxazepam (Serax™);
(e) antipsychotic medications: for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(f) mood stabilizers: such as carbamazepine (Tegretol™) and divalproex (Depakote™);
(g) nicotinic apha-7 agonists;
(h) mGluR5 antagonists;
(i) H3 agonists; and
(j) amyloid therapy vaccines.

Thus, in another embodiment, the invention provides a pharmaceutical composition comprising;
i) a compound of the invention, or a pharmaceutically acceptable salt thereof, and
ii) at least one compound selected from
    (a) acetylcholinesterase inhibitors,
    (b) glutamate antagonists, (c) antidepressant medications,
(d) anxiolytics,
(e) antipsychotic medications,
(f) mood stabilizers,
(g) nicotinic apha-7 agonists,
(h) mGluR5 antagonists,
(i) H3 agonists, and ii) one or more pharmaceutically acceptable excipient, diluent or carrier.

Consequently, the invention provides in further aspects
a pharmaceutical combination, e.g. for use in any of the methods described herein, comprising a therapeutically effective amount of a compound of the present invention, or a pharmaceutically acceptable salt thereof, and another therapeutic agent, for simultaneous or sequential administration.

a combination product comprising a compound of the present invention, or a pharmaceutically acceptable salt thereof, and another therapeutic agent.

a combination product comprising a compound of the present invention, or a pharmaceutically acceptable salt thereof, and another therapeutic agent as a combined preparation for use in therapy, e.g. for use in any of the therapies described herein. In one embodiment, the therapy is the treatment or prevention of cancer or a neurodegenerative disorder. In another embodiment, the therapy is the treatment or prevention of Parkinson's, Huntington's or Alzheimer's Disease. In yet another embodiment, the therapy is the treatment or prevention of Huntington's Disease.

a pharmaceutical composition comprising a compound of the present invention, or a pharmaceutically acceptable salt thereof, another therapeutic agent, and a pharmaceutically acceptable excipient, diluent or carrier.

a method as defined above comprising co-administration, e.g. concomitantly or in sequence, of a therapeutically effective amount of a compound of the present invention, or a pharmaceutically acceptable salt thereof, and another therapeutic agent, e.g. as indicated above.

a pharmaceutical combination, e.g. a kit, comprising a) a first agent which is a compound of the present invention as disclosed herein, or a pharmaceutically acceptable salt thereof, and b) another therapeutic agent, e.g. as indicated above; whereby such kit may comprise instructions for its administration.

The following examples of compounds of the present invention illustrate the invention. Methods for preparing such compounds are described hereinafter.

EXAMPLES

Abbreviations

EtOAc ethyl acetate
AcOH acetic acid
brs broad singlet
CDCl$_3$ deuterated chloroform
CsF cesium fluoride
d doublet
CH$_2$Cl$_2$ dichloromethane
DIPEA di-isopropylethyl amine
DMSO dimethylsulfoxide
DMSO-d$_6$ deuterated dimethylsulfoxide
dppf 1,1'-Bis(diphenylphosphino)ferrocene
EtOH ethanol
LC-MS liquid chromatography-mass spectrometry
MeOH methanol
m multiplet
MS mass spectrometry
NEt$_3$ triethylamine
NMR nuclear magnetic resonance
$^1$H NMR proton nuclear magnetic resonance
Pd(PPh$_3$)$_4$ tetrakis(triphenylphosphine)palladium
PPh$_3$ triphenyl phosphine
s singlet
TFA trifluoroacetic acid
THF tetrahydrofuran
UV ultraviolet
EtOH ethanol
CDCl$_3$ deuterated chloroform
SiO$_2$ silica gel
MgSO$_4$ magnesium sulfate
Na$_2$SO$_4$ sodium sulfate
Pd palladium
aq aqueous
TBME tertbutylmethylether
mL milliliter
LDA lithiumdiisopropylamine
Raney-Ni Raney-nickel
ax axial
eq equatorial
MHz megahertz
Rt retention time
Na$_2$S$_2$O$_3$ sodium thiosulfate Analytical Methods NMR: proton spectra are recorded on a Bruker Avance-spectrometer or Varian Oxford 400 spectrometer unless otherwise noted. Chemical shifts are reported in ppm relative to dimethyl sulfoxide ($\delta$ 2.50), or chloroform ($\delta$ 7.26). A small amount of the dry sample (2-5 mg) is dissolved in an appropriate deuterated solvent (1 mL).

LC/MS:

The sample is dissolved in suitable solvent such as MeCN, DMSO or MeOH and is injected directly into the column using an automated sample handler. The analysis is performed using one of the following methods:

LC-MS-Method 1

Column: Acquity HSS T3, 1.8 μm, 2.1×50 mm;

Eluent: Water (+0.05% formic acid+3.75 mM ammonium acetate):acetonitrile (+0.04% formic acid), from 98:2 to 2:98 in 1.4 min, hold 98% for 0.75 min;

Flow rate/Temperature: 1.2 ml/min at 50° C.

LC-MS-Method 2

Column: Machery-Nagel Nucleosil 100-3 C18 (70×4.6 mm);

Solvents/Gradient: A: 0.05% TFA in water; B: 0.05% TFA in acetonitrile; from 95% A/5% B to 5% A/95% B in 8 min.

Flow rate/Temperature: 1.4 ml/min at 45° C.

Synthesis of Amine Intermediates

The amine intermediates are either commercially available or may be prepared as described in the literature, or in an analogous manner, or can be prepared as described hereafter, or in an analogous manner.

Synthesis of Bicyclic Amine Intermediates

Bicyclic amine 1:
3-Hydroxy-8-aza-bicyclo[3.2.1]octane-8-carboxylic acid tert-butyl ester

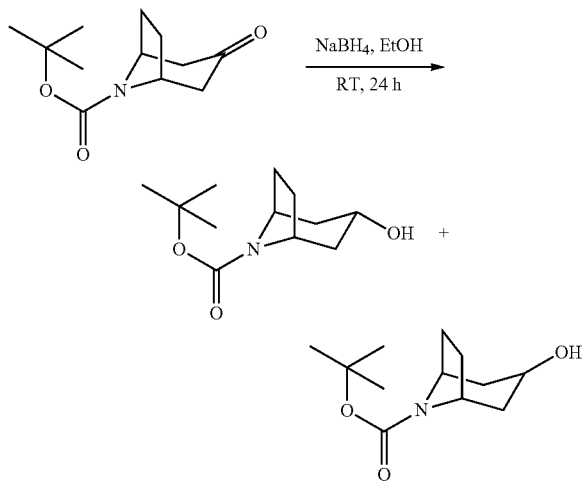

To a solution of 3-oxo-8-aza-bicyclo[3.2.1]octane-8-carboxylic acid tert-butyl ester (1.03 g, 4.57 mmol) in EtOH (20 mL) was added NaBH₄ dropwise. The mixture was stirred for 4.5 hours at room temperature under nitrogen, followed by a second addition of NaBH₄ (0.36 g, 9.60 mmol). The reaction was stirred at room temperature for 17.5 hours and a last addition of NaBH₄ (0.36 g, 9.60 mmol) was performed. The solution was stirred at room temperature for 2 hours, then a saturated solution of ammonium chloride was added and the aqueous phase was extracted with EtOAc. The combined organic fractions were dried over Na₂SO₄, filtered and concentrated. The crude was purified by flash chromatography on silica gel using cyclohexane/EtOAc as eluent to yield, after evaporation, to the axial and equatorial isomers (186 mg, 17.9%) and (205 mg, 19.7%) as white solids. 1H NMR (600 MHz, CDCl₃): 4.57 (d, 1H), 4.02 (m, 2H), 3.89 (d, 1 Hax), 1.89-1.71 (m, 5H), 1.65-1.54 (m, 1H), 1.47-1.28 (m, 11H) and 4.60 (d, 1H) 3.99 (m, 2H), 3.91 (m, 1 Heq), 2.18-2.03 (m, 2H), 1.92-1.72 (m, 4H), 1.67-1.56 (m, 2H), 1.39 (s, 9H)

Bicyclic amine 2: 8-Aza-bicyclo[3.2.1]octan-3-ol

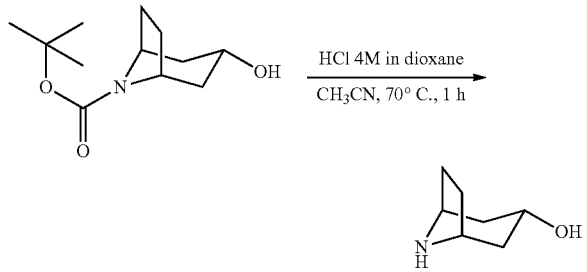

A solution of HCl (4N in dioxane, 0.82 mL, 3.27 mmol) was added to a suspension of 3-hydroxy-8-aza-bicyclo[3.2.1]octane-8-carboxylic acid tert-butyl ester in acetonitrile. The mixture was stirred at 70° C. for 1 hour, cooled down and concentrated. The product (138 mg, 93%) was isolated as a hydrochloric acid salt.

1H NMR (600 MHz, CDCl₃): 9.07-8.49 (m, 1H), 3.94 (m, 2H), 3.85 (m, 1H), 1.97-1.74 (m, 6H), 1.60 (t, 2H)

The axial isomer (137 mg, 93%) was prepared in the same way.

1H NMR (600 MHz, CDCl₃): 9.01-8.44 (m, 1H), 3.89 (m, 3H), 2.29 (d, 2H), 2.07 (dt, 2H), 1.96-1.84 (m, 2H), 1.83-1.71 (m, 2H)

Synthesis of Indole Intermediates

The indole intermediates are either commercially available or may be prepared as described in the literature, or in an analogous manner, or can be prepared as described hereafter, or in an analogous manner.

Indole 1: 4-Bromo-6-methoxy-1H-indole

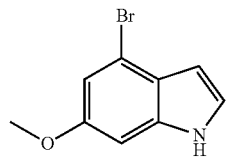

(a) N-(3-Bromo-5-methoxy-phenyl)-N-hydroxy-acetamide

3-Bromo-5-nitroanisole (1.5 g, 6.46 mmol) was dissolved in 20 mL of 1,2-dichloroethane and 20 mL of ethanol, and the mixture was cooled to 0° C. Raney-Ni (30 mg) and hydrazine hydrate (0.79 mL, 12.9 mmol) were added within 10 minutes, and the reaction was stirred for 4 hours at room temperature, when 50 mg of Raney-Ni were added. After stirring for 16 hours, another 50 mg of Raney-Ni were added, and after further stirring for 4 hours, another 50 mg of Raney-Ni were added. Stirring was continued for 4 hours at room temperature, when the starting material had completely disappeared. The reaction mixture was filtered through celite, and the solvent was removed under reduced pressure to provide N-(3-bromo-5-methoxy-phenyl)-N-hydroxylamine as a solid, which was dissolved in 80 ml of toluene. Sodium bicarbonate (597 mg, 7.11 mmol) was added, followed by acetyl chloride (0.51 mL, 7.11 mol). Stirring at room temperature was continued for 20 hours. The reaction mixture was then filtered and concentrated under reduced pressure. The residue was purified by column chromatography (40 g SiO₂; EtOAc/heptane in a gradient from 5/95 to 1/3) to yield the title compound as a solid (360 mg, 21% over 2 steps). LC-MS at 254 nm; [M+H] 260.0/262.1; Rt 0.82 min; (LCMS method 1).
¹H-NMR (600 MHz; DMSO-d⁶): 10.85 (brs, 1H), 7.50 (dd, 1H), 7.26 (dd, 1H), 6.94 (dd, 1H), 3.77 (s, 3H), 2.22 (s, 3H).

(b) 4-Bromo-6-methoxy-1H-indole

N-(3-Bromo-5-methoxy-phenyl)-N-hydroxy-acetamide (360 mg, 1.384 mmol) was dissolved in vinyl acetate (1.92 mL, 20.8 mmol), and Li₂PdCl₄ (18.2 mg, 69 μmol) was added. The reaction mixture was stirred for 3 hours at 60° C. The reaction mixture was diluted with EtOAc and brine; the organic layer was separated and concentrated under reduced pressure to give a solid, which was dissolved in 20 mL of MeOH. 1N aqueous NaOH (2.61 mL, 2.61 mmol) was added, and the reaction was stirred for two hours at room temperature. The reaction mixture was quenched by addition of 2 N aqueous HCl (1.3 mL, 2.6 mmol), followed by addition of 500 mg of $Na_2CO_3$. After addition of 50 mL of EtOAc, the organic layers were separated, dried over $Na_2SO_4$, filtered, and concentrated. The residue was purified by column chromatography (20 g $SiO_2$, EtOAc/heptane in a gradient from 0/100 to 1/4) to yield the title compound as a liquid (145 mg, 46% over 2 steps). $^1$H-NMR (600 MHz; DMSO-d$^6$): 11.26 (brs, 1H), 7.31 (dd, 1H), 6.93 (d, 1H), 6.90 (d, 1H), 6.29 (dd, 1H), 3.78 (s, 3H).

Indole 2: 4-Chloro-6-fluoro-1H-indole

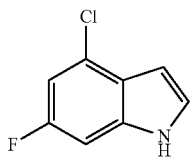 [SMILES: Fc1cc(Cl)c2cc[nH]c2c1]

(a) 1-Chloro-3-fluoro-5-nitro-benzene

Sodium perborate tetrahydrate (7.69 g, 50.0 mmol) was suspended in 30 mL of acetic acid, and this suspension was warmed to 55° C. 3-Chloro-5-fluoroaniline (1.46 g, 10 mmol) was dissolved in 20 mL of acetic acid and added within one hour. The reaction was stirred for 1 hour at 55° C. and then cooled to room temperature. 300 mL of TBME was added, and the reaction mixture was filtered. The organic layer was washed with brine, followed by 20 mL of aqueous $Na_2S_2O_3$, followed by brine. The organic layer was dried over $Na_2SO_4$ and concentrated under reduced pressure to give a residue, which was purified by column chromatography (40 g $SiO_2$; cyclohexane) to yield the title compound as a solid (320 mg, 18%). $^1$H-NMR (400 MHz; DMSO-d$^6$): 8.20 (s, 1H), 8.18 (d, 1H), 8.07 (d, 1H).

(b) N-(3-Chloro-5-fluoro-phenyl)-N-hydroxy-acetamide

1-Chloro-3-fluoro-5-nitro-benzene (320 mg, 1.82 mmol) was dissolved in 5 mL of 1,2-dichloroethane and 5 mL of ethanol, and the mixture was cooled to 0° C. Raney-Ni (30 mg, 2.0 mmol) and hydrazine hydrate (0.11 mL, 1.82 mmol) were added within 10 minutes, and the reaction was stirred for 4 hours at room temperature, when 50 mg of Raney-Ni were added. After stirring for 16 hours, another 50 mg of Raney-Ni were added, and after further stirring for 4 hours, another 50 mg of Raney-Ni were added. Stirring was continued for 4 hours at room temperature, when the starting material had completely disappeared. The reaction mixture was filtered through celite, and the solvent was removed under reduced pressure to provide N-(3-bromo-5-fluoro-phenyl)-N-hydroxylamine as a solid, which was dissolved in 15 ml of toluene. Sodium bicarbonate (160 mg, 1.91 mmol) was added, followed by acetyl chloride (136 µL, 1.91 mmol) in 0.5 mL of toluene. Stirring at room temperature was continued for 20 hours. The reaction mixture was then filtered and concentrated under reduced pressure. The residue was purified by column chromatography (40 g $SiO_2$; EtOAc/heptane in a gradient from 5/95 to 1/3) to yield the title compound as a solid (214 mg, 53% over 2 steps). LC-MS at 254 nm; [M+H] 204.1; Rt 0.83 min; (LCMS method 1). $^1$H-NMR (DMSO-d$^6$): 10.95 (s, 1H), 7.62 (s, 1H), 7.51 (dd, 1H), 7.19 (d, 1H), 2.24 (s, 3H).

(c) 4-Chloro-6-fluoro-1H-indole

N-(3-Chloro-5-fluoro-phenyl)-N-hydroxy-acetamide (200 mg, 982 µmol) was dissolved in vinyl acetate (1.81 mL, 19.6 mmol), and $Li_2PdCl_4$ (25.7 mg, 98 µmol) was added. The reaction mixture was stirred for 3 hr at 60° C. The reaction mixture was diluted with EtOAc and brine; the organic layer was separated and concentrated under reduced pressure to give a solid, which was dissolved in 8 mL of MeOH. 1N aqueous NaOH (1.89 mL, 1.89 mmol) was added, and the reaction was stirred for two hours at room temperature. The reaction mixture was quenched by addition of 2 N aqueous HCl (0.95 mL, 1.9 mmol), followed by addition of 300 mg of $Na_2CO_3$. After addition of 50 mL of EtOAc, the organic layers were separated, dried over $Na_2SO_4$, filtered, and concentrated. The residue was purified by column chromatography (12 g $SiO_2$; EtOAc/heptane in a gradient from 0/100 to 1/4) to yield the title compound as a liquid (72 mg, 45% over 2 steps). $^1$H-NMR (DMSO-d$^6$): 11.52 (brs, 1H), 7.45 (d, 1H), 7.20 (d, 1H), 7.05 (d, 1H), 6.45 (d, 1H).

Synthesis of Boronic Ester Intermediates

The boronic ester intermediates used in the preparation of compounds of the present invention are either commercially available or may be prepared as described in the literature, or in an analogous manner, or can be prepared as described hereafter, or in an analogous manner.

Boronic ester 1: 6-Methoxy-4-(4,4,5,5-tetramethyl-[1,3,2]dioxaborolan-2-yl)-1H-indole To a solution of 4-bromo-6-methoxy-1H-indole (200 mg, 885 µmol) in dioxane (5 mL) was added under argon bis(pinacolato)diboron (247 mg, 973 µmol) followed by tricyclohexylphosphine (14.9 mg, 53 µmol), bis(dibenzylideneacetone)Pd (15.3 mg, 27 µmol) and potassium acetate (130 mg, 1.33 mmol). The reaction mixture was stirred for 18 hours at 65° C. under argon. The reaction mixture was then diluted by addition of 30 ml of EtOAc and 20 ml of brine. The organic solvents were separated, dried over $Na_2SO_4$, filtered, and concentrated under reduced pressure. The residue was purified by column chromatography (20 g of $SiO_2$, tertbutylmethylether/heptane in a ratio of 3/7) to give the product (190 mg, 79%). $^1$H-NMR (DMSO-d$^6$): 10.89 (brs, 1H), 7.22 (dd, 1H), 7.03 (dd, 1H), 7.00 (d, 1H), 6.64 (dd, 1H), 3.77 (s, 3H), 1.33 (s, 12H).

Example 1

2,6-Bis-((R)-3-methyl-morpholin-4-yl)-8-pyridin-2-yl-9H-purine

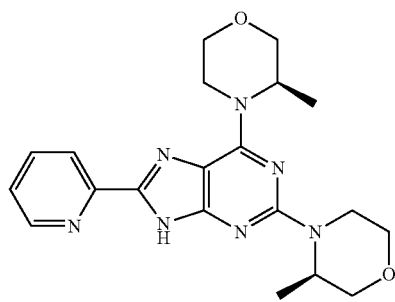 [SMILES: C[C@@H]1COCCN1c1nc(N2CCOC[C@H]2C)c2nc(-c3ccccn3)[nH]c2n1]

a) 2-Chloro-6-((R)-3-methyl-morpholin-4-yl)-9H-purine 2,6-Dichloro-9H-purine (2.36 g, 12.5 mmol), (R)-3-methylmorpholin hydrochloride (1.89 g, 13.8 mmol), and diisopropylethylamine (5.46 mL, 31.3 mmol) were dissolved in 15 mL of isopropanol, and the reaction mixture was stirred for 18 hours at 75° C. The reaction mixture was then diluted with 200 mL of $CH_2Cl_2$. The organic solvents were washed with aqueous $Na_2CO_3$, followed by water and brine. Drying over $Na_2SO_4$, filtering and concentration under reduced pressure gave a residue, which was purified by column chromatography (150 g $SiO_2$, $CH_2Cl_2$/EtOH/aq $NH_3$ in a ratio of 96/4/0.1) to give the product as a solid (2.87 g, 91%).

LC-MS at 254 nm; [M+H] 254.1/256.1; Rt 0.72 min; (LCMS method 1).

$^1$H NMR (DMSO-$d_6$): 13.25 (1H, brs), 8.17 (1H, s), 6.0-4.5 (brs, 2H), 4.0-3.0 (brs, 1H), 3.96 (dd, 1H), 3.76 (d, 1H), 3.67 (dd, 1H), 3.51 (ddd, 1H), 1.31 (d, 3H)

b) 2,6-Bis-((R)-3-methyl-morpholin-4-yl)-9H-purine

2-Chloro-6-((R)-3-methyl-morpholin-4-yl)-9H-purine (1.02 g, 4 mmol), diisopropylethylamine (1.40 mL, 8 mmol), and (R)-3-methylmorpholin hydrochloride (826 mg, 6 mmol) were stirred in 2-butanol (5 mL) in a closed microwave tube under argon at 50° C., until all ingredients were dissolved. The reaction was then stirred at 180° C. for 100 hours. The reaction mixture was then cooled to room temperature and diluted with 200 mL of $CH_2Cl_2$.

The organic layer was washed with aqueous $Na_2CO_3$ and brine. Drying over $Na_2SO_4$, filtering and concentration under reduced pressure gave a residue, which was purified by column chromatography (120 g $SiO_2$, $CH_2Cl_2$/EtOH/aqueous $NH_3$ in a gradient with a ratio from 100/0/0.1 to 94/6/0.1) to give the product as a foam (1.11 g, 87%).

LC-MS at 254 nm; [M+H] 319.0; Rt 0.71 min; (LCMS method 1).

$^1$H NMR (DMSO-$d_6$): 12.44 (s, 1H), 7.77 (s, 1H), 6.0-4.5 (brs, 2H), 4.51 (dd, 1H), 4.15 (dd, 1H), 4.0-3.0 (brs, 1H), 3.94 (dd, 1H), 3.89 (dd, 1H), 3.73 (d, 1H), 3.69 (d, 1H), 3.65 (dd, 1H), 3.58 (dd, 1H), 3.50 (ddd, 1H), 3.42 (dd, 1H), 3.07 (ddd, 1H), 1.27 (d, 3H) 1.15 (d, 3H).

c) 2,6-Bis-((R)-3-methyl-morpholin-4-yl)-9-(tetrahydro-pyran-2-yl)-9H-purine 2,6-Bis-((R)-3-methyl-morpholin-4-yl)-9H-purine (600 mg, 1.89 mmol) was dissolved in EtOAc (25 mL) under argon. After addition of 3,4-dihydro-2H-pyrane (172 µl, 1.89 mmol), trifluoro acetic acid anhydride (27 µl, 188 µmol), and trifluoro acetic acid (319 µl, 4.15 mmol), the reaction mixture was heated to 70° C. After 6 hours, 3,4-dihydro-2H-pyrane (1.44 mL, 15.7 mmol) was added. The reaction was then stirred for 22 hours at 70° C. and then cooled to room temperature. 500 mg of solid $Na_2CO_3$ was added and stirring continued for 10 minutes. The reaction mixture was diluted with EtOAc, the organic layer was separated, dried over $Na_2SO_4$, filtered and concentrated under reduced pressure to give a residue, which was purified by column chromatography (40 g $SiO_2$, heptane/EtOAc in a gradient from 9/1 to 2/3) to give the product as a foam (600 mg, 79%).

LC-MS at 254 nm; [M+H] 403.3; Rt 1.11 min; (LCMS method 1).

d) 8-Bromo-2,6-bis-((R)-3-methyl-morpholin-4-yl)-9-(tetrahydro-pyran-2-yl)-9H-purine Diisopropylamine (290 µl, 2.04 mmol) was dissolved in 4 mL of THF at −60° C., when butyllithium in hexane was added (1.27 mL, 2.04 mmol) to form LDA. 2,6-Bis-((R)-3-methyl-morpholin-4-yl)-9-(tetrahydro-pyran-2-yl)-9H-purine (585 mg, 1.45 mmol) was dissolved in 8 mL of THF and added to the reaction mixture at −78° C. within 10 minutes. The reaction was stirred for 1 hour at −78° C. Dibromotetrachloroethane (947 mg, 2.91 mmol) in 4 mL of THF was added within 10 minutes. The reaction was stirred for 2 hours at −78° C. The reaction was quenched by addition of saturated aqueous $NH_4Cl$ and warmed to room temperature. The mixture was diluted with 80 mL of EtOAc and 50 mL of brine. The organic layers were separated, dried over $Na_2SO_4$, filtered, and concentrated to give a residue, which was purified by column chromatography (30 g $SiO_2$, heptane/TBME in a ratio 7/3) to give the product as a foam (546 mg, 78%).

LC-MS at 254 nm; [M+H] 481.3/483.2; Rt 1.37 min; (LCMS method 1).

$^1$H NMR (DMSO-$d_6$): 5.50 (dd, 1H), 5.4-4.5 (brs, 2H), 4.48 (brs, 1H), 4.13 (dd, 1H), 4.01 (d, 1H), 3.93-3.87 (m, 2H), 3.74-3.66 (m, 2H), 3.64-3.55 (m, 3H), 3.5-3.0 (brs, 1H), 3.46 (ddd, 1H), 3.40 (dd, 1H), 3.11-3.03 (m, 1H), 3.00-2.90 (m, 1H), 1.96 (d, 1H), 1.78 (d, 1H), 1.70-1.48 (m, 3H), 1.24 (d, 3H), 1.14 (d, 3H).

e) 2,6-Bis-((R)-3-methyl-morpholin-4-yl)-8-pyridin-2-yl-9-(tetrahydro-pyran-2-yl)-9H-purine 8-Bromo-2,6-bis-((R)-3-methyl-morpholin-4-yl)-9-(tetrahydro-pyran-2-yl)-9H-purine (40 mg, 83 µmol) was dissolved in 2 mL of toluene under argon in a microwave vial, and 2-(tributylstannyl)-pyridine (36 mg, 83 µmol) and $Pd(PPh_3)_4$ (4.8 mg, 4.2 µmol) were added. The microwave vial was capped, and the reaction mixture was stirred for 3 hours at 120° C. The vial was cooled to room temperature and opened. The mixture was diluted with EtOAc (20 mL) and brine. The organic layer was separated, dried over $Na_2SO_4$, filtered and concentrated under reduced pressure. The residue was purified by column chromatography (12 g $SiO_2$, heptane/TBME in a gradient from 4/1 to 2/3) to give the product as a solid (35 mg, 88%).

LC-MS at 254 nm; [M+H] 480.3; Rt 1.34 min; (LCMS method 1).

$^1$H NMR (DMSO-$d_6$): 8.68 (d, 1H), 8.06 (d, 1H), 7.94 (dd, 1H), 7.46 (dd, 1H), 6.53 (dd, 1H), 6.0-4.5 (brs, 2H), 4.58-4.48 (m, 1H), 4.18 (dd, 1H), 3.99-3.86 (m, 3H), 3.78-3.69 (m, 2H), 3.69-3.64 (m, 1H), 3.64-3.56 (m, 1H), 3.5-3.0 (brs, 1H), 3.55-3.39 (m, 3H), 3.28-3.17 (m, 1H), 3.15-3.05 (m, 1H), 2.00-1.92 (m, 1H), 1.85 (dd, 1H), 1.65-1.45 (m, 3H), 1.28 (d, 3H), 1.18 (d, 3H).

f) 2,6-Bis-((R)-3-methyl-morpholin-4-yl)-8-pyridin-2-yl-9H-purine 2,6-Bis-((R)-3-methyl-morpholin-4-yl)-8-pyridin-2-yl-9-(tetrahydro-pyran-2-yl)-9H-purine (33 mg, 69 µmol) was dissolved in 3 mL of THF. 2N aqueous HCl (344 µl, 688 µmol) was added, and the reaction was stirred for 2 hours at room temperature. 100 mg of $Na_2CO_3$ and 10 mL of $CH_2Cl_2$ were added, and the reaction mixture was stirred for 20 minutes. The organic layer was separated, dried over $Na_2SO_4$, filtered, and concentrated under reduced pressure. The residue was purified by column chromatography (12 g $SiO_2$, heptane/EtOAc in a gradient from 100/0 to 3/2) to give the product as a solid (24 mg, 88%).

LC-MS at 254 nm; [M+H] 396.3; Rt 1.03 min; (LCMS method 1).

$^1$H NMR (DMSO-$d_6$): 12.98 (s, 1H), 8.62 (d, 1H), 8.12 (d, 1H), 7.89 (ddd, 1H), 7.40 (ddd, 1H), 6.0-4.5 (brs, 2H), 4.57

(dd, 1H), 4.20 (d, 1H), 4.0-3.0 (brs, 1H), 3.97 (dd, 1H), 3.89 (dd, 1H), 3.76 (d, 1H), 3.71-3.66 (m, 2H), 3.57 (dd, 1H), 3.53 (ddd, 1H), 3.41 (ddd, 1H), 3.09 (ddd, 1H), 1.30 (d, 3H) 1.17 (d, 3H)

Example 2

2-((S)-3-Methyl-morpholin-4-yl)-6-((R)-3-methyl-morpholin-4-yl)-8-(1H-pyrazol-3-yl)-9H-purine

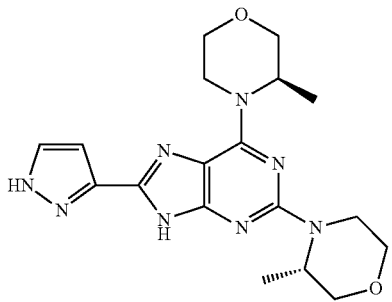 [SMILES: C[C@@H]1COCCN1c1nc(N2CCOC[C@@H]2C)nc2[nH]c(-c3cc[nH]n3)nc12]

a) 2-((S)-3-Methyl-morpholin-4-yl)-6-((R)-3-methyl-morpholin-4-yl)-9H-purine

2-Chloro-6-((R)-3-methyl-morpholin-4-yl)-9H-purine (712 mg, 2.81 mmol), diisopropylethylamine (0.98 mL, 5.61 mmol), and (S)-3-methylmorpholin hydrochloride (579 mg, 4.21 mmol) were stirred in 2-butanol (3 mL) in a closed 5 mL microwave tube under argon at 50° C., until all ingredients were dissolved. The reaction was then stirred at 175° C. for 48 hours. The organic layer was diluted with 200 mL of CH$_2$Cl$_2$ and washed with brine. Drying over Na$_2$SO$_4$, filtering and concentration under reduced pressure gave a residue, which was purified by column chromatography (40 g SiO$_2$, CH$_2$Cl$_2$/EtOH/aq NH$_3$ in a gradient from 100/0/0.1 to 90/10/0.1) to give the product as a solid (588 mg, 66%).

LC-MS at 254 nm; [M+H] 319.2; Rt 0.70 min; (LCMS method 1).

$^1$H NMR (DMSO-d$_6$): 12.42 (s, 1H), 7.75 (s, 1H), 6.0-4.5 (brs, 2H), 4.50 (dd, 1H), 4.09 (d, 1H), 4.0-3.0 (brs, 1H), 3.92 (dd, 1H), 3.87 (d, 1H), 3.71 (d, 1H), 3.67 (d, 1H), 3.64 (dd, 1H), 3.56 (dd, 1H), 3.48 (ddd, 1H), 3.40 (dd, 1H), 3.05 (ddd, 1H), 1.24 (d, 3H) 1.12 (d, 3H).

b) 8-Bromo-2-((S)-3-methyl-morpholin-4-yl)-6-((R)-3-methyl-morpholin-4-yl)-9H-purine 2-((S)-3-Methyl-morpholin-4-yl)-6-((R)-3-methyl-morpholin-4-yl)-9H-purine (786 mg, 2.47 mmol) were dissolved in CH$_2$Cl$_2$ (25 mL). Bromine (0.16 mL, 3.09 mmol) diluted in 2 mL of CH$_2$Cl$_2$ was added slowly within 2 minutes. The reaction mixture was stirred for 6 hours at room temperature. Aqueous Na$_2$S$_2$O$_3$ (10 mL) was added to the reaction mixture, and stirring was continued for 15 minutes. The organic layer was washed with brine and aqueous NaHCO$_3$. Drying over Na$_2$SO$_4$, filtering and concentration under reduced pressure gave a residue, which was purified by column chromatography (40 g SiO$_2$, heptane/EtOAc in a gradient from 2/3 to 4/1) to give the product as a foam (455 mg, 46%).

LC-MS at 254 nm; [M+H] 399.1/397.2; Rt 0.94 min; (LCMS method 1).

c) 2-((S)-3-Methyl-morpholin-4-yl)-6-((R)-methyl-morpholin-4-yl)-8-(1H-pyrazol-3-yl)-9H-purine 8-Bromo-2-((S)-3-methyl-morpholin-4-yl)-6-((R)-3-methyl-morpholin-4-yl)-9H-purine (50 mg, 126 µmol) was dissolved in dimethoxyethane (2 mL) and water (0.2 mL), followed by addition of 1H-pyrazole-3-ylboronic acid (21.1 mg, 189 µmol), PdCl$_2$(dppf) (9.21 mg, 13 µmol) and NEt$_3$ (53 µl, 378 µmol) under argon. The reaction mixture was heated to 85° C. for 23 hours. The reaction mixture was then diluted with EtOAc, the organic layer was separated, washed with brine, dried over MgSO$_4$, filtered and concentrated under reduced pressure. The residue was purified by column chromatography (12 g SiO$_2$, EtOAc) to give the product (19 mg, 39% yield).

LC-MS at 254 nm; [M+H] 385.3; Rt 0.81 min; (LCMS method 1).

$^1$H NMR (DMSO-d$_6$): 13.13 (s, 1H), 12.72 (s, 1H), 7.82 (s, 1H), 6.73 (s, 1H), 6.0-4.5 (brs, 2H), 4.54 (d, 1H), 4.13 (d, 1H), 4.0-3.0 (brs, 1H), 3.95 (d, 1H), 3.89 (d, 1H), 3.74 (d, 1H), 3.71-3.64 (m, 2H), 3.57 (d, 1H), 3.51 (dd, 1H), 3.41 (dd, 1H), 3.07 (dd, 1H), 1.26 (d, 3H) 1.15 (d, 3H)

Example 3

8-(1H-Indol-4-yl)-6-((R)-3-methyl-morpholin-4-yl)-2-[1,4]oxazepan-4-yl-9H-purine

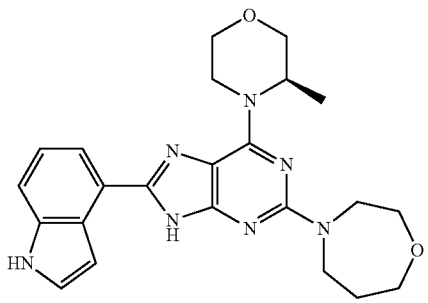 [SMILES: C[C@@H]1COCCN1c1nc(N2CCCOCC2)nc2[nH]c(-c3cccc4[nH]ccc34)nc12]

a) 8-Bromo-2-chloro-6-((R)-3-methyl-morpholin-4-yl)-9H-purine

To a solution of 2-chloro-6-((R)-3-methyl-morpholin-4-yl)-9H-purine (950 mg, 3.74 mmol) in CH$_2$Cl$_2$ (19 mL) was added bromine (0.23 mL, 4.49 mmol). The mixture was stirred at ambient temperature for 19 hours. Saturated sodium thiosulfate was added. The aqueous layer was extracted with dichloromethane two times. Organic layers were combined and dried over Na$_2$SO$_4$ and solvent was removed under reduced pressure. The crude was purified by flash column chromatography (0-70% EtOAc/cyclohexane gradient) to furnish product as a white solid (495 mg, 39%). LC-MS at 254 nm; [M+H] 334.1; Rt 0.89 min; (LCMS method 1).

$^1$H NMR (400 MHz, DMSO-d$_6$): 14.09 (br. s., 1H), 5.4-4.9 (m, 2H) 3.96 (d, 1H) 3.75 (d, 1H) 3.65 (dd, 1H) 3.42-3.57 (m, 1H), 3.41-3.37 (m, 1H), 1.29 (d, 3H)

b) 2-Chloro-8-(1H-indol-4-yl)-6-((R)-3-methyl-morpholin-4-yl)-9H-purine

In a sealed tube, to a solution of 8-bromo-2-chloro-6-((R)-3-methyl-morpholin-4-yl)-9H-purine (495 mg, 1.49 mmol)

in CH$_3$CN/H$_2$O (11/1.1 mL) was added cesium fluoride (452 mg, 2.98 mmol), indole-4-boronic acid (266 mg, 1.64 mmol), and tetrakis(triphenylphosphine)palladium (172 mg, 0.15 mmol). Then the reaction was conducted under microwave irradiation at 160° C. for 30 min. The solvents were removed under reduced pressure and the crude was purified by flash column chromatography (20-100% EtOAc/cyclohexane gradient) to provide 2-chloro-8-(1H-indol-4-yl)-6-((R)-3-methyl-morpholin-4-yl)-9H-purine (350 mg, 63.8%) as a pale yellow solid. LC-MS at 254 nm; [M+H] 369.2; Rt 1.00 min; (LCMS method 1). (400 MHz, DMSO-d$_6$): 13.59 (s, 1H), 11.41 (s, 1H), 7.73 (dd, 1H), 7.58-7.49 (m, 2H), 7.38-7.20 (m, 2H), 5.14 (s, 1H), 4.05-4.01 (m, 1H), 3.79-3.88 (m, 1H), 3.69-3.79 (m, 1H), 3.57 (s, 1H), 3.60 (s, 1H), 1.41 (d, 3H)

c) 8-(1H-Indol-4-yl)-6-((R)-3-methyl-morpholin-4-yl)-2-[1,4]oxazepan-4-yl-9H-purine To the solution of 2-chloro-8-(1H-indol-4-yl)-6-((R)-3-methyl-morpholin-4-yl)-9H-purine (50 mg, 0.14 mmol) in 1-butanol (300 μL) was added 1,4-oxazepane (20.6 mg, 0.20 mmol), followed by DIPEA (47.4 μL, 0.27 mmol). The mixture was stirred at 120° C. for 24 hours. Upon completion of the reaction, the solution was poured into water. The aqueous layer was extracted with CH$_2$Cl$_2$ three times. The combined organic layers were dried over Na$_2$SO$_4$, filtered, concentrated under reduced pressure and the crude was purified by flash column chromatography (30-100% EtOAc/cyclohexane gradient) to provide 2-((2S,6R)-2,6-dimethyl-morpholin-4-yl)-6-morpholin-4-yl-9H-purine (35 mg, 59%) as a beige solid. LC-MS at 254 nm; [M+H] 432.3; Rt 1.00 min; (LCMS method 1).
$^1$H NMR (400 MHz, DMSO-d$_6$) 12.47 (br. s., 1H), 11.00 (br. s., 1H), 7.67 (d, 1H), 7.43-7.39 (m, 2H), 7.28 (br. s., 1H), 7.16 (t, 1H), 5.45 (d, 1H), 5.08 (d, 1H), 4.10-3.95 (m, 1H), 3.91-3.85 (m, 4H), 3.82-3.75 (m, 4H), 3.69-3.65 (m, 2H), 3.63-3.57 (m, 1H), 3.48-3.40 (m, 1H), 1.98-1.90 (m, 2H), 1.23-1.18 (m, 3H)μ

Example 4

8-[4-(1H-Imidazol-2-yl)-phenyl]-2,6-bis-((R)-3-methyl-morpholin-4-yl)-9H-purine

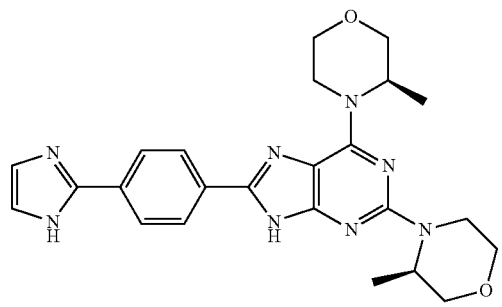 [SMILES: C[C@@H]1COCCN1c1nc(N2CCOC[C@H]2C)c2nc(-c3ccc(-c4ncc[nH]4)cc3)[nH]c2n1]

a) 8-Bromo-2,6-bis-((R)-3-methyl-morpholin-4-yl)-9H-purine 2,6-Bis-((R)-3-methyl-morpholin-4-yl)-9H-purine (637 mg, 2 mmol) was dissolved in 50 mL of CH$_2$Cl$_2$ and stirred under argon. Bromine (124 μl, 2.4 mmol) was dissolved in 2 mL of CH$_2$Cl$_2$ and added within 2 minutes. The reaction was stirred for 6 hours at room temperature. 5 mL of aqueous Na$_2$S$_2$O$_3$ were added, the mixture was stirred for 15 minutes, and the organic solvents were separated, washed with brine and aqueous NaHCO$_3$, dried over Na$_2$SO$_4$, filtered, and concentrated. The residue was purified by column chromatography (40 g SiO$_2$, heptane/EtOAc in a gradient from 2/3 to 4/1) to give a foam (422 mg, 53%).
$^1$H NMR (DMSO-d$_6$): 13.20 (1H, brs), 5.4-4.5 (brs, 2H), 4.48 (d, 1H), 4.12 (d, 1H), 3.93 (d, 1H), 3.89 (dd, 1H), 3.73 (d, 1H), 3.68 (d, 1H), 3.64 (d, 1H), 3.56 (dd, 1H), 3.48 (ddd, 1H), 3.41 (ddd, 1H), 3.4-3.1 (brs, 1H), 3.07 (ddd, 1H), 1.26 (d, 3H), 1.15 (d, 3H)

b) 8-[4-(1H-Imidazol-2-yl)-phenyl]-2,6-bis-((R)-3-methyl-morpholin-4-yl)-9H-purine 8-Bromo-2,6-bis-((R)-3-methyl-morpholin-4-yl)-9H-purine (99 mg, 250 μmol) was dissolved in 2 mL of acetonitrile and 0.2 mL of water under argon. 4-(1H-imidazol-2-yl)phenyl boronic acid (58.7 mg, 313 μmol), CsF (57 mg, 375 μmol), and Pd(PPh$_3$)$_4$ (28.9 mg, 25 μmol) were added. The suspension was stirred at 50° C. for 10 minutes in a closed microwave vial. Then it was irradiated for 40 minutes in a microwave apparatus at 150° C. The vial was cooled and uncapped, and the reaction mixture was diluted with 50 mL of CH$_2$Cl$_2$ and 10 mL of isopropanol. The organic solvents were washed with brine and aqueous NaHCO$_3$, dried over Na$_2$SO$_4$, filtered and concentrated under reduced pressure. The residue was purified by column chromatography (40 g SiO$_2$, CH$_2$Cl$_2$/EtOH/aqueous NH$_3$ in a gradient from 100/0/0.1 to 90/10/0.1) to give the product as a solid (58 mg, 48%).
LC-MS at 254 nm; [M+H] 461.3; Rt 0.76 min; (LCMS method 1). 1H NMR (600 MHz, DMSO-d$_6$): 13.03 (s, 1H), 12.62 (s, 1H), 8.10 (d, 2H), 8.02 (d, 2H), 7.31 (s, 1H), 7.07 (s, 1H), 6.0-4.5 (brs, 2H), 4.55 (dd, 1H), 4.20 (d, 1H), 4.0-3.0 (brs, 1H), 3.99 (dd, 1H), 3.92 (dd, 1H), 3.79 (d, 1H), 3.74-3.68 (m, 2H), 3.61 (dd, 1H), 3.55 (ddd, 1H), 3.45 (ddd, 1H), 3.12 (ddd, 1H), 1.32 (d, 3H), 1.19 (d, 3H)

Example 5

8-(6-Fluoro-1H-indol-4-yl)-2-((S)-3-methyl-morpholin-4-yl)-6-((R)-3-methyl-morpholin-4-yl)-9H-purine

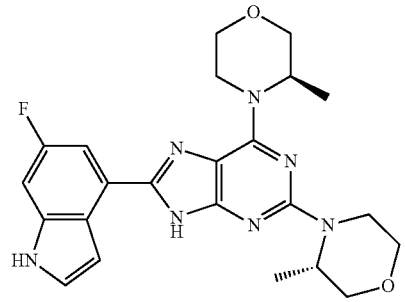 [SMILES: C[C@@H]1COCCN1c1nc(N2CCOC[C@@H]2C)nc2[nH]c(-c3cc(F)cc4[nH]ccc34)nc12]

4-Chloro-6-fluoro-1H-indole (72 mg, 0.42 mmol) was dissolved in 4 mL of dioxane under argon. Bis(pinacolato)diboron (198 mg, 778 μmol), tricyclohexylphospine (19.8 mg, 71 μmol), bis(dibenzylidenacetone)palladium (20.3 mg, 35 μmol), and potassium acetate (104 mg, 1.06 mmol) were added under argon. The reaction was stirred for 24 hours at 80° C. The reaction mixture was cooled to room temperature and diluted with 30 mL of EtOAc. The organic layer was washed with 20 mL of brine, dried over Na$_2$SO$_4$, filtered, and concentrated under reduced pressure. The residue was filtered through a column (40 g SiO$_2$; EtOAc/heptane in a gradient from 0/100 to 12/88) to yield a mixture, which was concentrated under reduced pressure, and then dissolved in 2 mL of acetonitrile and 0.2 mL of water under argon. 8-Bromo-2-((S)-3-methylmorpholin-4-yl-)-6-((R)-3-methyl-morpholin-4-yl)-9H-purine (100 mg, 153 µmol) was added, followed by cesium fluoride (25.8 mg, 170 µmol) and tetrakis(triphenylphospine)palladium (26 mg, 23 µmol). The reaction mixture was stirred at 135° C. for 2 hours in a sealed vial. The reaction mixture was cooled to room temperature and diluted with 40 mL of EtOAc. The organic layer was washed with brine, dried over Na$_2$SO$_4$, filtered, and concentrated. The residue was purified by column chromatography (10 g SiO$_2$; tertbutylmethylether) to give the title compound as a foam (36 mg, 19% over 2 steps).

LC-MS at 254 nm; [M+H] 452.3; Rt 1.06 min; (LCMS method 1).

$^1$H-NMR (400 MHz; DMSO-d$^6$): 12.95 (s, 1H), 11.33 (s, 1H), 7.57 (d, 1H), 7.45 (s, 1H), 7.25 (s, 1H), 7.23 (d, 1H), 6.0-4.5 (brs, 2H), 4.56 (d, 1H), 4.17 (d, 1H), 4.0-3.0 (brs, 1H), 4.00 (d, 1H), 3.91 (d, 1H), 3.80 (d, 1H), 3.75-3.68 (m, 2H), 3.60 (d, 1H), 3.57 (dd, 1H), 3.44 (dd, 1H), 3.11 (ddd, 1H), 1.35 (d, 3H), 1.18 (d, 3H).

Example 6

{4-[2,6-Bis-((R)-3-methyl-morpholin-4-yl)-9H-purin-8-yl]-1H-indol-6-yl}-methanol

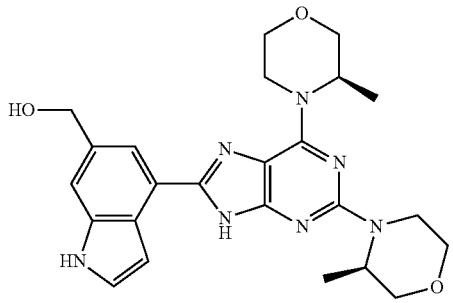 [SMILES: C[C@@H]1COCCN1c1nc(N2CCOC[C@H]2C)c2nc(-c3cc(CO)cc4[nH]ccc34)[nH]c2n1]

4-[2,6-Bis-((R)-3-methyl-morpholin-4-yl)-9H-purin-8-yl]-1H-indole-6-carboxylic acid methyl ester (example 32, 72 mg, 146 µmol) was dissolved in 10 ml THF under argon. 1N LiAlH$_4$ in THF (0.22 mL, 0.22 mmol) was added at 5° C., and the reaction was stirred for 2 hours at room temperature. The reaction was quenched by addition of aqueous saturated Na$_2$SO$_4$ (1 mL). The mixture was diluted with 30 mL of CH$_2$Cl$_2$ and 3 mL of isopropanol. The organic phases were separated, dried over Na$_2$SO$_4$, filtered, and concentrated. The residue was purified by column chromatography (12 g SiO$_2$, CH$_2$Cl$_2$/EtOH in a gradient from 100/0 to 88/12) to give the product as a solid (58 mg, 84%).

LC-MS at 254 nm; [M+H] 464.3; Rt 0.88 min; (LCMS method 1).

1H NMR (600 MHz, DMSO-d$_6$): 12.83 (s, 1H), 11.22 (s, 1H), 7.63 (d, 1H), 7.44 (s, 1H), 7.40 (dd, 1H), 7.18 (dd, 1H), 6.0-4.5 (brs, 2H), 5.16 (t, 1H), 4.61 (d, 2H), 4.55 (dd, 1H), 4.19 (d, 1H), 4.0-3.0 (brs, 1H), 3.99 (dd, 1H), 3.90 (dd, 1H), 3.79 (d, 1H), 3.74-3.68 (m, 2H), 3.59 (dd, 1H), 3.56 (ddd, 1H), 3.44 (ddd, 1H), 3.10 (ddd, 1H), 1.35 (d, 3H), 1.17 (d, 3H)

Examples 7 to 32

Examples 7 to 9 in Table 2 below can be made using procedures analogous to those described in Example 1 using the appropriate boronic acid or boronic ester intermediate.

Examples 10 to 11 in Table 2 below can be made using procedures analogous to those described in Example 2 using the appropriate boronic acid or boronic ester intermediate.

Examples 12 to 26 in Table 2 below can be made using procedures analogous to those described in Example 3 using the appropriate boronic acid or boronic ester intermediate.

Examples 27 to 32 in Table 2 below can be made using procedures analogous to those described in Example 4 using the appropriate boronic acid or boronic ester intermediate.

| Example Number | Structure and Name | $^1$H NMR | LC/MS |
|---|---|---|---|
| 7 | 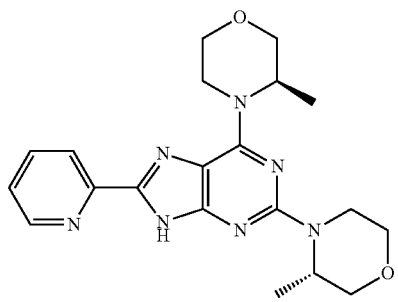<br>2-((S)-3-Methyl-morpholin-4-yl)-6-((R)-3-methyl-morpholin-4-yl)-8-pyridin-2-yl-9H-purine | 1H NMR (600 MHz, DMSO-d$_6$): 13.00 (s, 1H), 8.64 (d, 1H), 8.14 (d, 1H), 7.91 (ddd, 1H), 7.42 (ddd, 1H), 6.0-4.5 (brs, 2H), 4.59 (dd, 1H), 4.19 (d, 1H), 4.0-3.0 (brs, 1H), 3.99 (dd, 1H), 3.91 (dd, 1H), 3.79 (d, 1H), 3.73-3.68 (m, 2H), 3.59 (dd, 1H), 3.56 (ddd, 1H), 3.43 (ddd, 1H), 3.11 (ddd, 1H), 1.31 (d, 3H) 1.18 (d, 3H) | Method 1 Retention Time: 1.06 min Mass (ES+): 396.4 |

-continued

| Example Number | Structure and Name | $^1$H NMR | LC/MS |
|---|---|---|---|
| 8 | 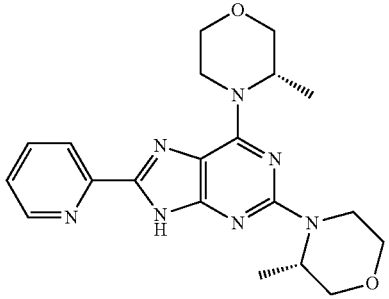<br>2,6-Bis-((S)-3-methyl-morpholin-4-yl)-8-pyridin-2-yl-9H-purine | 1H NMR (600 MHz, DMSO-$d_6$): 12.99 (s, 1H), 8.62 (d, 1H), 8.12 (d, 1H), 7.89 (ddd, 1H), 7.40 (ddd, 1H), 6.0-4.5 (brs, 2H), 4.56 (dd, 1H), 4.19 (d, 1H), 4.0-3.0 (brs, 1H), 3.96 (dd, 1H), 3.89 (dd, 1H), 3.76 (d, 1H), 3.71-3.66 (m, 2H), 3.57 (dd, 1H), 3.53 (ddd, 1H), 3.41 (ddd, 1H), 3.09 (ddd, 1H), 1.30 (d, 3H) 1.16 (d, 3H) | Method 1 Retention Time: 1.04 min Mass (ES+): 396.4 |
| 9 | 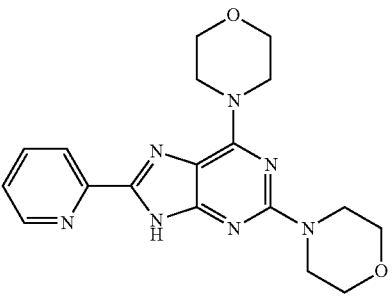<br>2,6-Di-morpholin-4-yl-8-pyridin-2-yl-9H-purine | | Method 2 Retention Time: 4.38 min Mass (ES+): 367.95 |
| 10 | 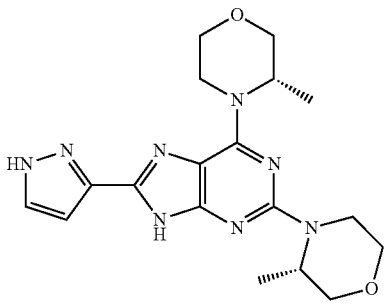<br>2,6-Bis-((S)-3-methyl-morpholin-4-yl)-8-(1H-pyrazol-3-yl)-9H-purine | 1H NMR (400 MHz, DMSO-$d_6$): 13.13 (s, 1H), 12.72 (s, 1H), 7.84 (dd, 1H), 6.75 (dd, 1H), 6.0-4.5 (brs, 2H), 4.6-4.47 (m, 1H), 4.16 (dd, 1H), 4.0-3.0 (brs, 1H), 3.96 (dd, 1H), 3.90 (dd, 1H), 3.76 (d, 1H), 3.73-3.64 (m, 2H), 3.59 (dd, 1H), 3.52 (dd, 1H), 3.43 (dd, 1H), 3.09 (dd, 1H), 1.29 (d, 3H) 1.17 (d, 3H) | Method 1 Retention Time: 0.81 min Mass (ES+): 385.3 |
| 11 | 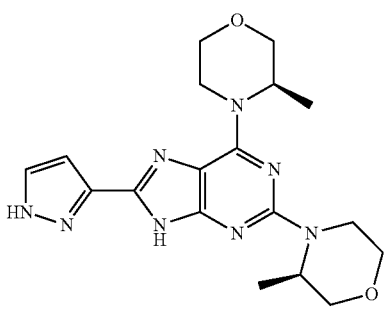<br>2,6-Bis-((R)-3-methyl-morpholin-4-yl)-8-(1H-pyrazol-3-yl)-9H-purine | 1H NMR (600 MHz, DMSO-$d_6$): 13.12 (s, 1H), 12.71 (s, 1H), 7.82 (d, 1H), 6.74 (d, 1H), 6.0-4.5 (brs, 2H), 4.52 (d, 1H), 4.16 (d, 1H), 4.0-3.0 (brs, 1H), 3.95 (d, 1H), 3.88 (d, 1H), 3.74 (d, 1H), 3.71-3.63 (m, 2H), 3.57 (d, 1H), 3.51 (dd, 1H), 3.41 (dd, 1H), 3.08 (ddd, 1H), 1.27 (d, 3H), 1.15 (d, 3H) | Method 1 Retention Time: 0.81 min Mass (ES+): 385.3 |

| Example Number | Structure and Name | ¹H NMR | LC/MS |
|---|---|---|---|
| 12 | 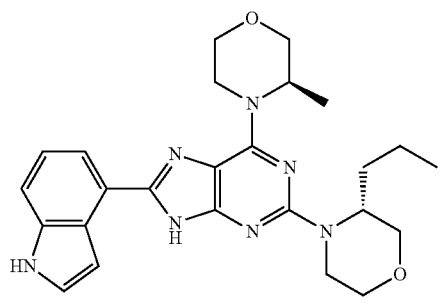<br>8-(1H-Indol-4-yl)-6-((R)-3-methyl-morpholin-4-yl)-2-((R)-3-propyl-morpholin-4-yl)-9H-purine | ¹H NMR (600 MHz, DMSO-$d_6$): 12.77 (br. s., 1H), 11.28 (br. s., 1H), 7.66 (d, 1H), 7.46-7.43 (m, 2H), 7.25 (t, 1H), 7.15 (t, 1H), 5.6-5.4 (s, 1H), 5.1-4.8 (m, 1H), 4.49 (t, 1H), 4.27 (d, 1H), 3.98 (dd, 1H), 3.85 (dd, 1H), 3.79 (d, 2H), 3.72 (d, 1H), 3.59-3.48 (m, 2H), 3.45-3.35 (m, 1H), 3.31 (br. s., 1H), 3.10 (td, 1H), 1.75-1.68 (m, 1H), 1.60-1.53 (m, 1H), 1.37-1.20 (m, 5H), 0.89 (t, 3H) | Method 1<br>Retention Time: 1.17 min<br>Mass (ES+): 462.3 |
| 13 | 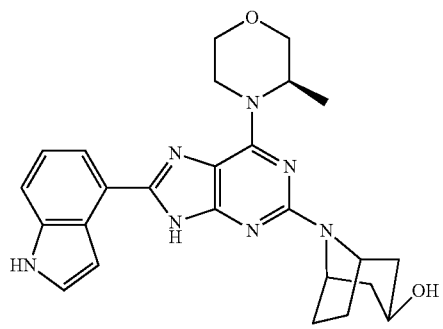<br>8-[8-(1H-Indol-4-yl)-6-((R)-3-methyl-morpholin-4-yl)-9H-purin-2-yl]-8-aza-bicyclo[3.2.1]octan-3-ol | ¹H NMR (400 MHz, DMSO-$d_6$): 12.93 (s, 1H), 11.28 (br. s., 1H), 7.67 (d, 1H), 7.56-7.44 (m, 2H), 7.28 (br. s., 1H), 7.16 (t, 1H), 5.5-5.0 (m, 1H), 4.56 (br. s., 2H), 4.36 (d, 1H), 4.07-3.95 (m, 3H), 3.84-3.71 (m, 2H), 3.62-3.55 (m, 1H), 1.94 (d, 2H), 1.82-1.66 (m, 4H), 1.66-1.49 (m, 2H), 1.45-1.31 (m, 3H) | Method 1<br>Retention Time: 0.85 min<br>Mass (ES+): 460.4 |
| 14 | 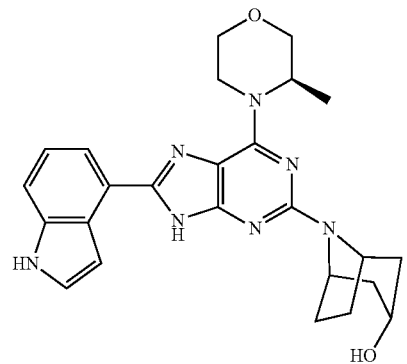<br>8-[8-(1H-Indol-4-yl)-6-((R)-3-methyl-morpholin-4-yl)-9H-purin-2-yl]-8-aza-bicyclo[3.2.1]octan-3-ol | ¹H NMR(400 MHz, DMSO-$d_6$): 12.87 (s, 1H), 11.28 (br. s., 1H), 7.66 (d, 1H), 7.50-7.40 (m, 2H), 7.30-7.25 (m, 1H), 7.16 (t, 1H), 5.6-5.0 (m, 1H), 4.58-4.46 (m, 3H), 4.07-3.94 (m, 2H), 3.88 (br. s., 1H), 3.85-3.68 (m, 2H), 3.58 (t, 1H), 3.44-3.40 (m, 1H), 2.26 (d, 2H), 2.14-2.06 (d, 2H), 2.94-1.79 (m, 2H), 1.65-1.57 ( m, 2H), 1.36 (d, 3H) | Method 1<br>Retention Time: 0.86 min<br>Mass (ES+): 460.3 |

| Example Number | Structure and Name | ¹H NMR | LC/MS |
|---|---|---|---|
| 15 | 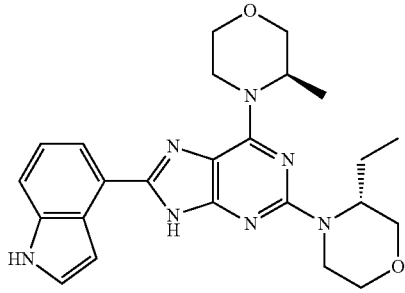<br>2-((R)-3-Ethyl-morpholin-4-yl)-8-(1H-indol-4-yl)-6-((R)-3-methyl-morpholin-4-yl)-9H-purine | ¹H NMR (600 MHz, DMSO-$d_6$): 12.79 (s, 1H), 11.27 (br. s., 1H), 7.66 (d, 1H), 7.48-7.42 (m, 2H), 7.25 (br. s., 1H), 7.14 (t, 1H), 5.7-4.7 (m, 2H), 4.37 (t, 1H), 4.27 (d, 1H), 3.99 (dd, 1H), 3.88-3.77 (m, 3H), 3.72 (d, 1H), 3.62-3.47 (m, 2H), 3.42 (td, 2H), 3.12-3.06 (m, 1H), 1.79-1.72 (m, 1H), 1.63-1.56 (m, 1H), 1.40-1.29 (m, 3H), 0.87 (t, 3H) | Method 1<br>Retention Time: 1.07 min<br>Mass (ES+): 448.3 |
| 16 | 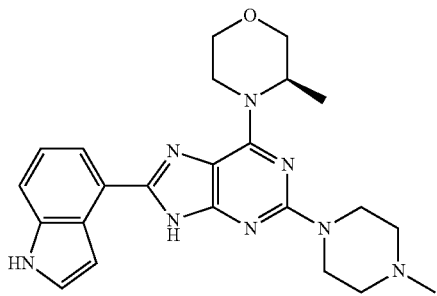<br>8-(1H-Indol-4-yl)-6-((R)-3-methyl-morpholin-4-yl)-2-(4-methyl-piperazin-1-yl)-9H-purine | ¹H NMR (600 MHz, DMSO-$d_6$) 12.81 (s, 1H), 11.28 (br. s., 1H), 7.65 (d, 1H), 7.53-7.43 (m, 2H), 7.25 (t, 1H), 7.15 (t, 1H), 5.6-5.0 (m, 2H), 3.99 (dd, 1H), 3.82-3.76 (m, 1H), 3.75-3.65 (m, 3H), 3.58-3.53 (m, 1H), 3.49-3.46 (m, 1H), 3.40 (t, 1H), 3.34-3.29 (m, 1H), 2.39-2.27 (m, 4H), 2.26-2.10 (m, 3H), 1.34 (d, 3H) | Method 1<br>Retention Time: 0.69 min<br>Mass (ES+): 433.3 |
| 17 | 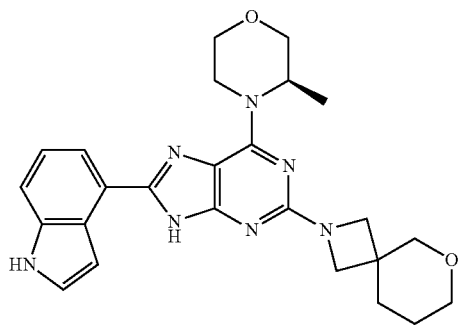<br>8-(1H-Indol-4-yl)-6-((R)-3-methyl-morpholin-4-yl)-2-(6-oxa-2-aza-spiro[3.5]non-2-yl)-9H-purine | ¹H NMR (600 MHz, DMSO-$d_6$): 12.95 (s, 1H), 11.28 (br. s., 1H), 7.63-7.60 (m, 1H), 7.46-7.40 (m, 2H), 7.25 (t, 1H), 7.14 (t, 1H), 5.65-4.85 (m, 2H), 4.00-3.95 (m, 1H), 3.81-3.75 (m, 1H), 3.73-3.66 (m, 3H), 3.65-3.59 (m, 4H), 3.57-3.44 (m, 3H), 3.42-3.38 (m, 1H), 1.83-1.68 (m, 2H), 1.55-1.43 (m, 2H), 1.34 (d, 3H) | Method 1<br>Retention Time: 0.97 min<br>Mass (ES+): 460.3 |

-continued

| Example Number | Structure and Name | ¹H NMR | LC/MS |
|---|---|---|---|
| 18 | 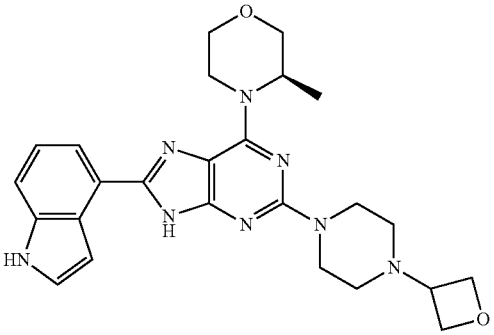<br>8-(1H-Indol-4-yl)-6-((R)-3-methyl-morpholin-4-yl)-2-(4-oxetan-3-yl-piperazin-1-yl)-9H-purine | ¹H NMR (600 MHz, DMSO-$d_6$): 12.83 (s, 1H), 11.28 (br. s., 1H), 7.64 (d, 1H), 7.50-7.42 (m, 2H), 7.25 (br. s., 1H), 7.15 (t, 1H), 5.75-4.70 (m, 2H), 4.55 (t, 2H), 4.47 (t, 2H), 3.99 (dd, 1H), 3.81-3.76 (m, 1H), 3.75-3.64 (m, 5H), 3.62-3.51 (m, 1H), 3.46-3.38 (m, 2H), 2.30 (t, 4H), 1.34 (d, 3H) | Method 1<br>Retention Time: 0.72 min<br>Mass (ES+): 475.3 |
| 19 | 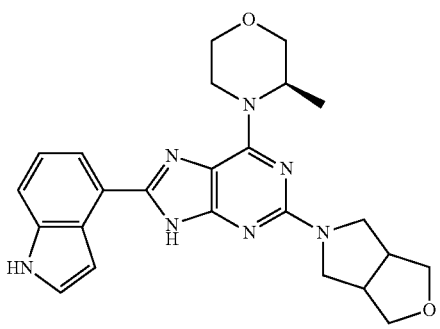<br>8-(1H-Indol-4-yl)-6-((R)-3-methyl-morpholin-4-yl)-2-(tetrahydro-furo[3,4-c]pyrrol-5-yl)-9H-purine | ¹H NMR (400 MHz, DMSO-$d_6$): 12.89 (s, 1H), 11.28 (br. s., 1H), 7.68-7.64 (m, 1H), 7.48-7.44 (m, 2H), 7.28 (t, 1H), 7.16 (t, 1H), 5.7-4.2 (m, 2H), 4.01 (dd, 1H), 3.89-3.79 (m, 3H), 3.77-3.66 (m, 3H), 3.62-3.55 (m, 3H), 3.54-3.42 (m, 2H), 3.32 (s, 1H), 3.02-2.91 (m, 2H), 1.37 (d, 3H) | Method 1<br>Retention Time: 0.88 min<br>Mass (ES+): 446.3 |
| 20 | 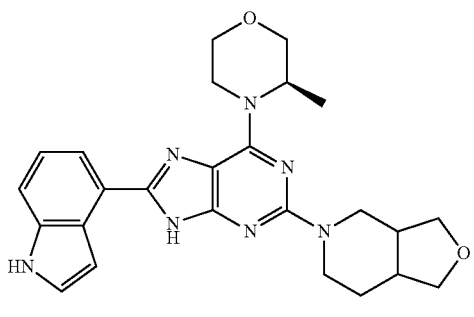<br>2-(Hexahydro-furo[3,4-c]pyridin-5-yl)-8-(1H-indol-4-yl)-6-((R)-3-methyl-morpholin-4-yl)-9H-purine | ¹H NMR (400 MHz, DMSO-$d_6$): 12.81 (s, 1H), 11.29 (br. s., 1H), 7.69-7.64 (m, 1H), 7.49-7.44 (m, 2H), 7.27 (br. s., 1H), 7.16 (t, 1H), 5.6-4.8 (m, 2H), 3.98-3.90 (m, 1H), 3.84-3.71 (m, 6H), 3.62-3.54 (m, 2H), 3.48-3.39 (m, 3H), 3.33-3.30 (m, 1H), 2.49-2.33 (m, 2H), 1.77 (br. s., 1H), 1.52 (br. s., 1H), 1.36 (d, 3H) | Method 1<br>Retention Time: 0.95 min<br>Mass (ES+): 460.3 |
| 21 | 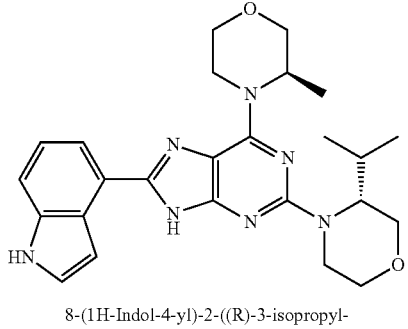<br>8-(1H-Indol-4-yl)-2-((R)-3-isopropyl-morpholin-4-yl)-6-((R)-3-methyl-morpholin-4-yl)-9H-purine | ¹H NMR (600 MHz, DMSO-$d_6$): 12.75 (s, 1H), 11.27 (br. s., 1H), 7.64 (d, 1H), 7.38-7.45 (m, 2H), 7.24 (t, 1H), 7.14 (t, 1H), 5.2-4.7 (m, 2H), 4.45 (d, 1H), 4.29 (d, 1H), 3.98-3.92 (m, 2H), 3.84-3.78 (m, 2H), 3.74-3.69 (m, 1H), 3.60-3.53 (m, 1H), 3.43-3.35 (m, 2H), 3.32-3.21 (m, 1H), 3.09 (td, 1H), 2.48-2.30 (m, 1H), 1.34 (d, 3H), 1.00 (d, 3H), 0.77 (d, 3H) | Method 1<br>Retention Time: 1.12 min<br>Mass (ES+): 462.3 |

| Example Number | Structure and Name | ¹H NMR | LC/MS |
|---|---|---|---|
| 22 | 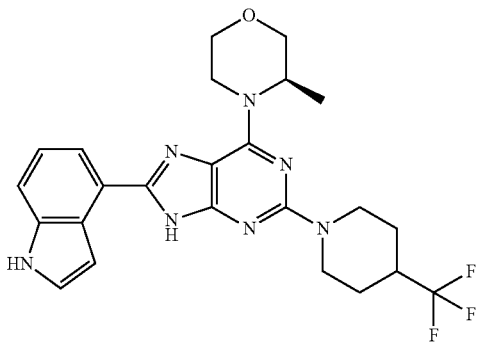<br>8-(1H-Indol-4-yl)-6-((R)-3-methyl-morpholin-4-yl)-2-(4-trifluoromethyl-piperidin-1-yl)-9H-purine | ¹H NMR (600 MHz, DMSO-$d_6$): 12.84 (br. s., 1H), 11.28 (br. s., 1H), 7.65 (d, 1H), 7.47-7.43 (m, 2H), 7.25 (br. s., 1H), 7.15 (t, 1H), 5.7-5.3 (m, 1H), 4.75 (d, 2H), 4.00 (d, 1H), 3.82-3.77 (m, 1H), 3.76-3.70 (m, 1H), 3.57 (t, 1H), 3.37 (br. s., 1H), 2.86 (t, 2H), 2.64-2.56 (m, 1H), 1.83 (d, 2H), 1.43-1.36 (m, 3H), 1.34 (d, 3H) | Method 1 Retention Time: 1.24 min Mass (ES+): 486.3 |
| 23 | 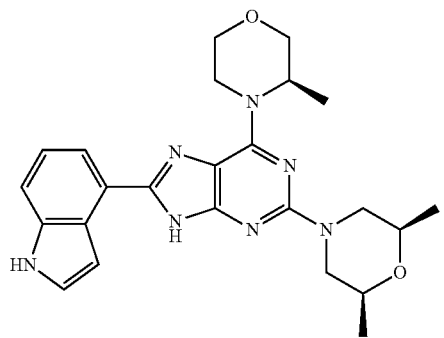<br>2-((2S,6R)-2,6-Dimethyl-morpholin-4-yl)-8-(1H-indol-4-yl)-6-((R)-3-methyl-morpholin-4-yl)-9H-purine | ¹H NMR (600 MHz, DMSO-$d_6$): 12.83 (br. s., 1H), 11.28 (br. s., 1H), 7.65 (d, 1H), 7.53-7.42 (m, 2H), 7.25 (br. s., 1H), 7.15 (t, 1H), 5.5-5.0 (m, 2H), 4.42 (d, 2H), 4.00 (d, 1H), 3.80 (d, 1H), 3.73 (d, 1H), 3.60-3.52 (m, 3H), 3.3 (m, 1H), 2.48-2.43 (m, 2H), 1.35 (d, 3H), 1.15 (d, 6H) | Method 1 Retention Time: 1.1 min Mass (ES+): 448.3 |
| 24 | 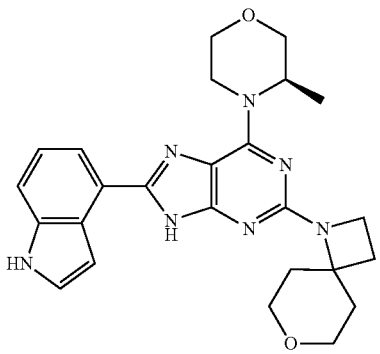<br>8-(1H-Indol-4-yl)-6-((R)-3-methyl-morpholin-4-yl)-2-(7-oxa-1-aza-spiro[3.5]non-1-yl)-9H-purine | ¹H NMR (600 MHz, CHLOROFORM-d): 8.42 (br. s., 1H), 7.55 (d, 1H), 7.49 (d, 1H) 7.38 (br. s., 1H), 7.31-7.26 (m, 2H), 4.17-4.07 (m, 3H), 4.01 (dd, 3H), 3.88 (d, 2H), 3.77-3.64 (m, 3H), 3.43 (t, 3H), 2.73 (br. s., 2H), 2.25 (t, 2H), 1.76 (d, 2H), 1.51 (br. s., 3H) | Method 1 Retention Time: 0.92 min Mass (ES+): 460.3 |

| Example Number | Structure and Name | ¹H NMR | LC/MS |
|---|---|---|---|
| 25 | 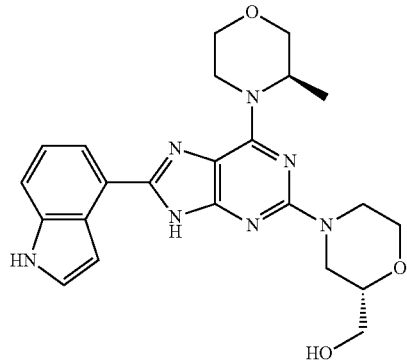<br>{(S)-4-[8-(1H-Indol-4-yl)-6-((R)-3-methyl-morpholin-4-yl)-9H-purin-2-yl]-morpholin-2-yl}-methanol | ¹H NMR (600 MHz, DMSO-$d_6$): 12.87 (s, 1H), 11.28 (br. s., 1H), 7.65 (d, 1H), 7.45 (d, 2H), 7.25 (br. s., 1H), 7.15 (t, 1H), 5.7-4.9 (m, 2H), 4.80 (t, 1H), 4.53 (d, 1H), 4.36 (d, 1H), 4.00 (d, 1H), 3.91 (d, 1H), 3.80 (d, 1H), 3.73 (d, 1H), 3.60-3.46 (m, 3H), 3.44-3.36 (m, 3H), 2.90 (t, 1H), 2.58-2.64 (m, 1H), 1.35 (d, 3H) | Method 1 Retention Time: 0.82 min Mass (ES+): 450.3 |
| 26 | 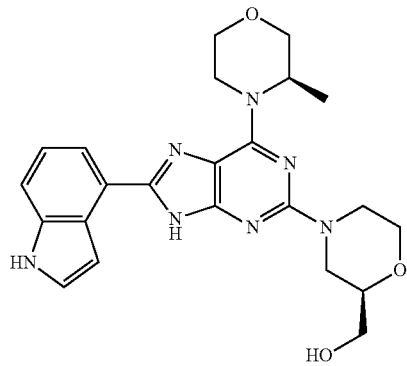<br>{(R)-4-[8-(1H-Indol-4-yl)-6-((R)-3-methyl-morpholin-4-yl)-9H-purin-2-yl]-morpholin-2-yl}-methanol | ¹H NMR (600 MHz, DMSO-$d_6$): 12.86 (s, 1H), 11.28 (br. s., 1H), 7.65 (d, 1H), 7.55-7.43 (m, 2H), 7.27-7.23 (m, 1H), 7.15 (t, 1H), 5.7-5.0 (m, 2H), 4.81 (t, 1H), 4.52 (d, 1H), 4.42-4.32 (m, 1H), 3.99 (d, 1H), 3.91 (d, 1H), 3.80 (d, 1H), 3.73 (d, 1H), 3.56-3.38 (m, 6H), 2.93-2.86 (m, 1H), 2.64-2.58 (m, 1H), 1.33 (d, 3H) | Method 1 Retention Time: 0.83 min Mass (ES+): 450.3 |
| 27 | 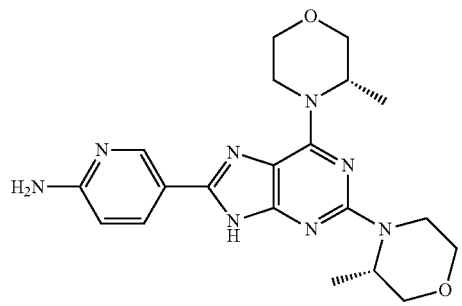<br>5-[2,6-Bis-((S)-3-methyl-morpholin-4-yl)-9H-purine-8-yl]-pyridin-2-ylamine | 1H NMR (600 MHz, DMSO-$d_6$): 12.72 (s, 1H), 8.58 (d, 1H), 7.97 (dd, 1H), 6.51 (d, 1H), 6.36 (s, 2H), 6.0-4.5 (brs, 2H), 4.52 (dd, 1H), 4.16 (dd, 1H), 4.0-3.0 (brs, 1H), 3.96 (dd, 1H), 3.90 (dd, 1H), 3.76 (d, 1H), 3.72-3.64 (m, 2H), 3.60 (dd, 1H), 3.52 (ddd, 1H), 3.44 (ddd, 1H), 3.09 (ddd, 1H), 1.29 (d, 3H) 1.17 (d, 3H) | Method 1 Retention Time: 0.73 min Mass (ES+): 411.3 |

| Example Number | Structure and Name | ¹H NMR | LC/MS |
|---|---|---|---|
| 28 | 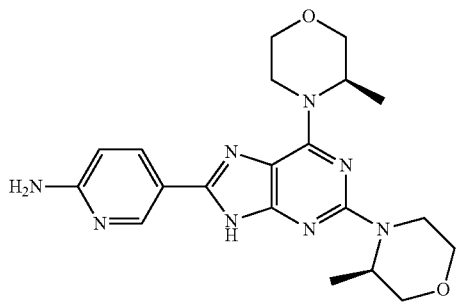<br>5-[2,6-Bis-((R)-3-methyl-morpholin-4-yl)-9H-purine-8-yl]-pyridin-2-ylamine | 1H NMR (600 MHz, DMSO-d$_6$): 12.72 (s, 1H), 8.58 (d, 1H), 7.97 (dd, 1H), 6.51 (d, 1H), 6.36 (s, 2H), 6.0-4.5 (brs, 2H), 4.52 (dd, 1H), 4.16 (dd, 1H), 4.0-3.0 (brs, 1H), 3.96 (dd, 1H), 3.90 (dd, 1H), 3.76 (d, 1H), 3.72-3.64 (m, 2H), 3.60 (dd, 1H), 3.52 (ddd, 1H), 3.44 (ddd, 1H), 3.09 (ddd, 1H), 1.29 (d, 3H) 1.17 (d, 3H) | Method 1<br>Retention Time: 0.73 min<br>Mass (ES+): 411.3 |
| 29 | 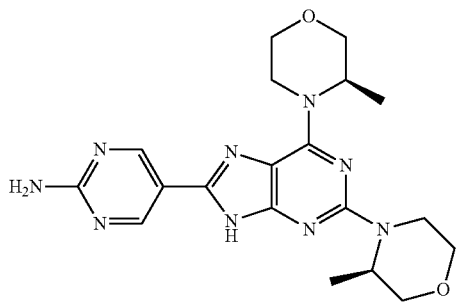<br>5-[2,6-Bis-((R)-3-methyl-morpholin-4-yl)-9H-purine-8-yl]-pyrimidin-2-yl-amine | H NMR (600 MHz, DMSO-d$_6$): 12.84 (s, 1H), 8.80 (s, 2H), 7.08 (s, 2H), 6.0-4.5 (brs, 2H), 4.49 (dd, 1H), 4.14 (d, 1H), 4.0-3.0 (brs, 1H), 3.94 (dd, 1H), 3.88 (dd, 1H), 3.74 (d, 1H). 3.71-3.63 (m, 2H), 3.58 (dd, 1H), 3.50 (ddd, 1H), 3.42 (ddd, 1H), 3.07 (ddd, 1H), 1.27 (d, 3H) 1.15 (d, 3H) | Method 1<br>Retention Time: 0.78 min<br>Mass (ES+): 412.3 |
| 30 | 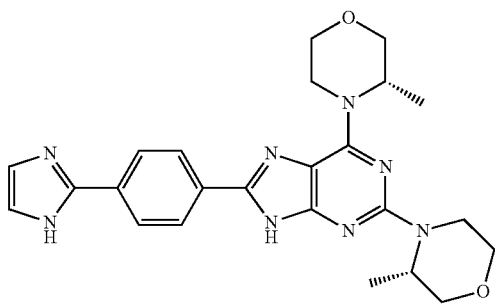<br>8-[4-(1H-Imidazol-2-yl)-phenyl]-2,6-bis-((S)-3-methyl-morpholin-4-yl)-9H-purine | 1H NMR (600 MHz, DMSO-d$_6$): 13.82 (brs, 1H), 13.11 (s, 1H), 8.17 (d, 2H), 8.05 (d, 2H), 7.47 (s, 2H), 6.0-4.5 (brs, 2H), 4.55 (dd, 1H), 4.20 (d, 1H), 4.0-3.0 (brs, 1H), 3.99 (dd, 1H), 3.92 (dd, 1H), 3.79 (d, 1H), 3.74-3.66 (m, 2H), 3.61 (dd, 1H), 3.55 (ddd, 1H), 3.45 (ddd, 1H), 3.12 (ddd, 1H), 1.33 (d, 3H), 1.19 (d, 3H) | Method 1<br>Retention Time: 0.76 min<br>Mass (ES+): 461.3 |
| 31 | 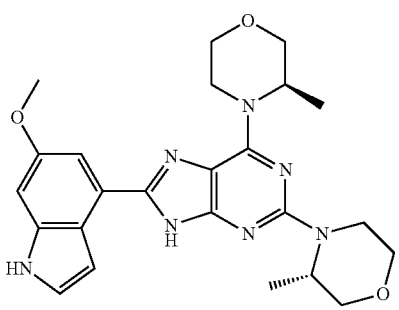<br>8-(6-Methoxy-1H-indol-4-yl)-2-((S)-3-methyl-morpholin-4-yl)-6-((R)-3-methyl-morpholin-4-yl)-9H-purine | 1H NMR (600 MHz, DMSO-d$_6$): 12.87 (s, 1H), 11.04 (s, 1H), 7.39 (d, 1H), 7.29 (dd, 1H), 7.14 (s, 1H), 6.96 (s, 1H), 6.0-4.5 (brs, 2H), 4.56 (d, 1H), 4.16 (d, 1H), 4.0-3.0 (brs, 1H), 3.99 (d, 1H), 3.90 (dd, 1H), 3.82 (s, 3H), 3.79 (d, 1H), 3.75-3.67 (m, 2H), 3.60 (dd, 1H), 3.56 (dd, 1H), 3.44 (dd, 1H), 3.10 (ddd, 1H), 1.34 (d, 3H), 1.17 (d, 3H). | Method 1<br>Retention Time: 1.02 min<br>Mass (ES+): 464.3 |

| Example Number | Structure and Name | ¹H NMR | LC/MS |
|---|---|---|---|
| 32 | 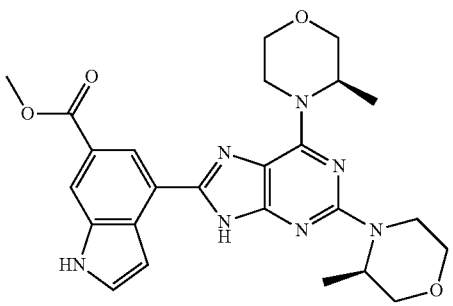<br>4-[2,6-Bis-((R)-3-methyl-morpholin-4-yl)-9H-purin-8-yl]-1H-indol-6-carboxylic acid methyl ester | 1H NMR (400 MHz, DMSO-$d_6$): 13.11 (s, 1H), 11.70 (s, 1H), 8.34 (d, 1H), 8.09 (s, 1H), 7.71 (dd, 1H), 7.32 (dd, 1H), 6.0-4.5 (brs, 2H), 4.56 (dd, 1H), 4.19 (d, 1H), 4.0-3.0 (brs, 1H), 3.99 (dd, 1H), 3.90 (dd, 1H), 3.89 (s, 3H), 3.79 (d, 1H), 3.75-3.68 (m, 2H), 3.60 (dd, 1H), 3.56 (ddd, 1H), 3.44 (ddd, 1H), 3.11 (ddd, 1H), 1.36 (d, 3H), 1.18 (d, 3H) | Method 1 Retention Time: 1.05 min Mass (ES+): 492.3 |

The invention claimed is:

1. A compound of formula (I), or a pharmaceutically acceptable salt thereof,

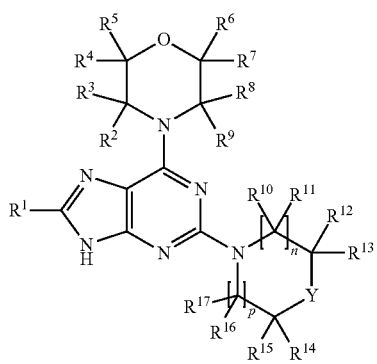

wherein $R^1$ is selected from the group consisting of

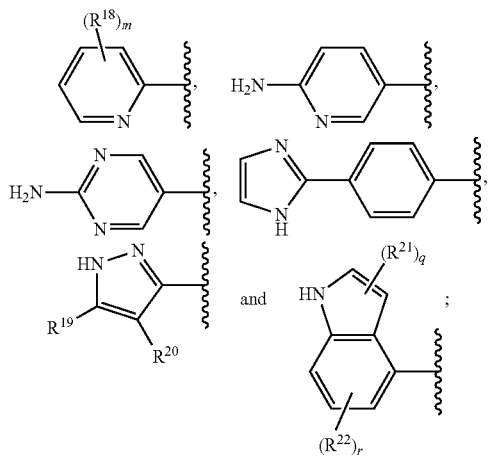

wherein $R^{18}$ on each occurrence independently represents fluoro or methyl;

m represents 0, 1, 2 or 3;

$R^{19}$ and $R^{20}$ independently represent hydrogen or fluoro;

$R^{21}$ represents fluoro;

$R^{22}$ on each occurrence independently represents fluoro, methoxy, hydroxymethyl or methoxycarbonyl;

q represents 0, 1 or 2 and r represents 0, 1, 2 or 3 provided that q+r is not 0;

$R^2$, $R^3$, $R^4$, $R^5$, $R^6$, $R^7$, $R^8$ and $R^9$ independently represent hydrogen, $C_{1-3}$alkyl or fluoro-$C_{1-3}$alkyl; or $R^3$ and $R^6$ together form a methylene bridge; or $R^3$ and $R^8$ together form an ethylene bridge; or $R^5$ and $R^6$ together form an ethylene bridge;

n and p independently represent 0, 1 or 2;

$R^{10}$, $R^{11}$, $R^{12}$, $R^{13}$, $R^{14}$, $R^{15}$, $R^{16}$ and $R^{17}$ on each occurrence independently represent hydrogen, $C_{1-3}$alkyl, fluoro-$C_{1-3}$alkyl or hydroxy-$C_{1-3}$alkyl; or $R^{11}$ and $R^{16}$ together form an ethylene bridge; or $R^{13}$ and $R^{14}$ together form an ethylene bridge; or $R^{14}$ and $R^{15}$, together with the carbon atom to which they are attached, are linked to form a tetrahydropyranyl ring; and Y represents O, $CHR^{23}$, $CR^{24}R^{25}$ or $NR^{26}$, wherein $R^{23}$ represents hydroxyl or fluoro-$C_{1-3}$alkyl; or $R^{23}$ and $R^{13}$, together with the carbon atoms to which they are attached, are linked to form a fused tetrahydrofuranyl ring;

$R^{24}$ and $R^{25}$ independently represent hydrogen or halogen; or $R^{24}$ and $R^{25}$, together with the carbon atom to which they are attached, are linked to form a tetrahydropyranyl ring; and $R^{26}$ represents $C_{1-3}$alkyl or oxetanyl;

and a compound, or a pharmaceutically acceptable salt thereof, selected from the following list of compounds:

8-(1H-Indol-4-yl)-6-(3-methyl-morpholin-4-yl)-2-[1,4]oxazepan-4-yl-9H-purine;

8-[8-(1H-Indol-4-yl)-6-(3-methyl-morpholin-4-yl)-9H-purin-2-yl]-8-aza-bicyclo[3.2.1] octan-3-ol;

8-[8-(1H-Indol-4-yl)-6-(3-methyl-morpholin-4-yl)-9H-purin-2-yl]-8-aza-bicyclo[3.2.1]octan-3-ol;

8-(1H-Indol-4-yl)-6-(3-methyl-morpholin-4-yl)-2-(4-methyl-piperazin-1-yl)-9H-purine;

8-(1H-Indol-4-yl)-6-(3-methyl-morpholin-4-yl)-2-(6-oxa-2-aza-spiro[3.5]non-2-yl)-9H-purine;

8-(1H-Indol-4-yl)-6-(3-methyl-morpholin-4-yl)-2-(4-oxetan-3-yl-piperazin-1-yl)-9H-purine;

8-(1H-Indol-4-yl)-6-(3-methyl-morpholin-4-yl)-2-(tetrahydro-furo[3,4-c]pyrrol-5-yl)-9H-purine;

2-(Hexahydro-furo[3,4-c]pyridin-5-yl)-8-(1H-indol-4-yl)-6-(3-methyl-morpholin-4-yl)-9H-piperidinpurine;

8-(1H-Indol-4-yl)-6-(3-methyl-morpholin-4-yl)-2-(7-oxa-1-aza-spiro[3.5]non-1-yl)-9H-purine;

{4-[8-(1H-Indol-4-yl)-6-(3-methyl-morpholin-4-yl)-9H-purin-2-yl]-morpholin-2-yl}-methanol.

2. A compound according to claim 1, or a pharmaceutically acceptable salt thereof, wherein $R^1$ represents

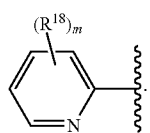

3. A compound according to claim 1, or a pharmaceutically acceptable salt thereof, wherein $R^1$ represents

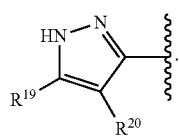

4. A compound according to claim 1, or a pharmaceutically acceptable salt thereof, wherein $R^1$ represents

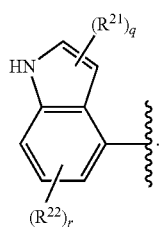

5. A compound according to claim 1, or a pharmaceutically acceptable salt thereof, wherein $R^2$, $R^3$, $R^4$, $R^5$, $R^6$, $R^7$, $R^8$ and $R^9$ independently represent hydrogen or methyl; or $R^3$ and $R^6$ together form a methylene bridge; or $R^3$ and $R^8$ together form an ethylene bridge; or $R^5$ and $R^6$ together form an ethylene bridge.

6. A compound according to claim 1, or a pharmaceutically acceptable salt thereof, wherein Y represents O.

7. A compound according to claim 1, or a pharmaceutically acceptable salt thereof, wherein Y represents $CHR^{23}$ or $CR^{24}R^{25}$.

8. A compound, or a pharmaceutically acceptable salt thereof, according to claim 1 which is selected from:
2,6-Bis-((R)-3-methyl-morpholin-4-yl)-8-pyridin-2-yl-9H-purine;
2-((S)-3-Methyl-morpholin-4-yl)-6-((R)-3-methyl-morpholin-4-yl)-8-(1H-pyrazol-3-yl)-9H-purine;
8-(1H-Indol-4-yl)-6-((R)-3-methyl-morpholin-4-yl)-2-[1,4]oxazepan-4-yl-9H-purine;
8-[4-(1H-Imidazol-2-yl)-phenyl]-2,6-bis-((R)-3-methyl-morpholin-4-yl)-9H-purine;
8-(6-Fluoro-1H-indol-4-yl)-2-((S)-3-methyl-morpholin-4-yl)-6-((R)-3-methyl-morpholin-4-yl)-9H-purine;
{4-[2,6-Bis-((R)-3-methyl-morpholin-4-yl)-9H-purin-8-yl]-1H-indol-6-yl}-methanol;
2-((S)-3-Methyl-morpholin-4-yl)-6-((R)-3-methyl-morpholin-4-yl)-8-pyridin-2-yl-9H-purine;
2,6-Bis-((S)-3-methyl-morpholin-4-yl)-8-pyridin-2-yl-9H-purine;
2,6-Di-morpholin-4-yl-8-pyridin-2-yl-9H-purine;
2,6-Bis-((S)-3-methyl-morpholin-4-yl)-8-(1H-pyrazol-3-yl)-9H-purine;
2,6-Bis-((R)-3-methyl-morpholin-4-yl)-8-(1H-pyrazol-3-yl)-9H-purine;
8-[8-(1H-Indol-4-yl)-6-((R)-3-methyl-morpholin-4-yl)-9H-purin-2-yl]-8-aza-bicyclo[3.2.1]octan-3-ol;
8-[8-(1H-Indol-4-yl)-6-((R)-3-methyl-morpholin-4-yl)-9H-purin-2-yl]-8-aza-bicyclo[3.2.1]octan-3-ol;
8-(1H-Indol-4-yl)-6-((R)-3-methyl-morpholin-4-yl)-2-(4-methyl-piperazin-1-yl)-9H-purine;
8-(1H-Indol-4-yl)-6-((R)-3-methyl-morpholin-4-yl)-2-(6-oxa-2-aza-spiro[3.5]non-2-yl)-9H-purine;
8-(1H-Indol-4-yl)-6-((R)-3-methyl-morpholin-4-yl)-2-(4-oxetan-3-yl-piperazin-1-yl)-9H-purine;
8-(1H-Indol-4-yl)-6-((R)-3-methyl-morpholin-4-yl)-2-(tetrahydro-furo[3,4-c]pyrrol-5-yl)-9H-purine;
2-(Hexahydro-furo[3,4-c]pyridin-5-yl)-8-(1H-indol-4-yl)-6-((R)-3-methyl-morpholin-4-yl)-9H-purine;
8-(1H-Indol-4-yl)-6-((R)-3-methyl-morpholin-4-yl)-2-(7-oxa-1-aza-spiro[3.5]non-1-yl)-9H-purine;
{(S)-4-[8-(1H-Indol-4-yl)-6-((R)-3-methyl-morpholin-4-yl)-9H-purin-2-yl]-morpholin-2-yl}-methanol;
{(R)-4-[8-(1H-Indol-4-yl)-6-((R)-3-methyl-morpholin-4-yl)-9H-purin-2-yl]-morpholin-2-yl}-methanol;
5-[2,6-Bis-((S)-3-methyl-morpholin-4-yl)-9H-purin-8-yl]-pyridin-2-ylamine;
5-[2,6-Bis-((R)-3-methyl-morpholin-4-yl)-9H-purin-8-yl]-pyridin-2-ylamine;
5-[2,6-Bis-((R)-3-methyl-morpholin-4-yl)-9H-purin-8-yl]-pyrimidin-2-yl-amine;
8-[4-(1H-Imidazol-2-yl)-phenyl]-2,6-bis-((S)-3-methyl-morpholin-4-yl)-9H-purine;
8-(6-Methoxy-1H-indol-4-yl)-2-((S)-3-methyl-morpholin-4-yl)-6-((R)-3-methyl-morpholin-4-yl)-9H-purine;
4-[2,6-Bis-((R)-3-methyl-morpholin-4-yl)-9H-purin-8-yl]-1H-indole-6-carboxylic acid methyl ester; and
pharmaceutically acceptable salts thereof.

9. A compound according to claim 1 which is 2,6-Bis-((R)-3-methyl-morpholin-4-yl)-8-pyridin-2-yl-9H-purine having the following formula

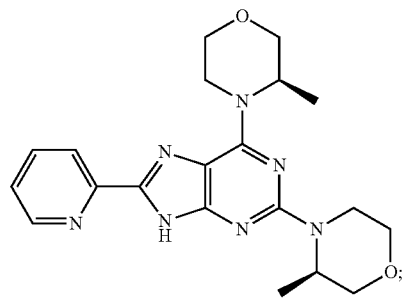 [SMILES: C[C@@H]1COCCN1c1nc(N2CCOC[C@H]2C)c2nc(-c3ccccn3)[nH]c2n1]

or a pharmaceutically acceptable salt thereof.

10. A compound according to claim 1 which is 8-(6-Fluoro-1H-indol-4-yl)-2-((S)-3-methyl-morpholin-4-yl)-6-((R)-3-methyl-morpholin-4-yl)-9H-purine having the following formula

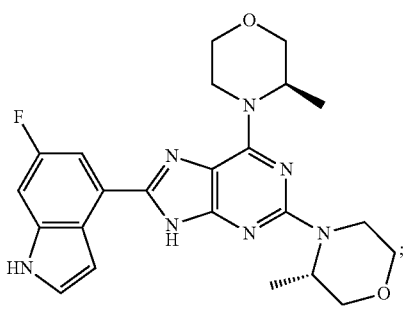 [SMILES: C[C@@H]1COCCN1c1nc(N2CCOC[C@@H]2C)nc2[nH]c(-c3cc(F)cc4[nH]ccc34)nc12]

or a pharmaceutically acceptable salt thereof.

11. A compound according to claim 1 which is 2-((S)-3-Methyl-morpholin-4-yl)-6-((R)-3-methyl-morpholin-4-yl)-8-pyridin-2-yl-9H-purine having the following formula

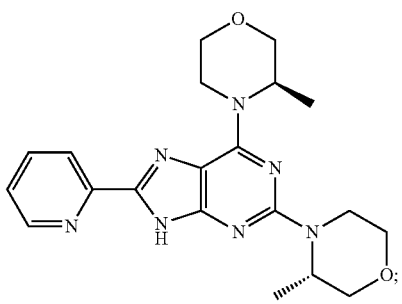 [SMILES: C[C@@H]1COCCN1c1nc(N2CCOC[C@@H]2C)nc2[nH]c(-c3ccccn3)nc12]

or a pharmaceutically acceptable salt thereof.

12. A compound according to claim 1 which is 2,6-Bis-((S)-3-methyl-morpholin-4-yl)-8-(1H-pyrazol-3-yl)-9H-purine having the following formula

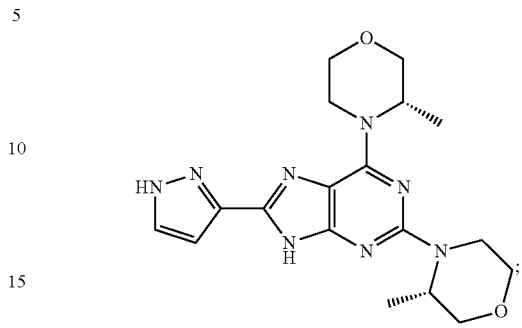

or a pharmaceutically acceptable salt thereof.

13. A pharmaceutical composition comprising a compound according claim 1, or a pharmaceutically acceptable salt thereof, and a pharmaceutically acceptable excipient, diluent or carrier.

14. A method for the treatment of a disease or disorder modulated by the inhibition of the mTor enzyme, comprising administration of a compound according to claim 1, or a pharmaceutically acceptable salt thereof, to a subject in need thereof wherein the disease or disorder is cancer, a neurodegenerative disorder or an ophthalmological disease.

15. A combination product comprising a compound according to claim 1, or a pharmaceutically acceptable salt thereof, and another therapeutic agent.

* * * * *

SEQUENCE LISTING

```
<160> NUMBER OF SEQ ID NOS: 1

<210> SEQ ID NO 1
<211> LENGTH: 615
<212> TYPE: PRT
<213> ORGANISM: Artificial Sequence
<220> FEATURE:
<223> OTHER INFORMATION: Fusion protein used for autophagy assay
<220> FEATURE:
<221> NAME/KEY: mCherry
<222> LOCATION: (1)..(236)
<220> FEATURE:
<221> NAME/KEY: GFP
<222> LOCATION: (241)..(479)
<220> FEATURE:
<221> NAME/KEY: LC3A
<222> LOCATION: (495)..(615)

<400> SEQUENCE: 1

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160
```

```
Ala Leu Lys Gly Glu Ile Lys Gln Arg Leu Lys Leu Lys Asp Gly Gly
            165                 170                 175

His Tyr Asp Ala Glu Val Lys Thr Thr Tyr Lys Ala Lys Lys Pro Val
        180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
        210                 215                 220

Arg His Ser Thr Gly Gly Met Asp Glu Leu Tyr Lys Pro Val Ala Thr
225                 230                 235                 240

Met Val Ser Lys Gly Glu Glu Leu Phe Thr Gly Val Val Pro Ile Leu
                245                 250                 255

Val Glu Leu Asp Gly Asp Val Asn Gly His Lys Phe Ser Val Ser Gly
            260                 265                 270

Glu Gly Glu Gly Asp Ala Thr Tyr Gly Lys Leu Thr Leu Lys Phe Ile
        275                 280                 285

Cys Thr Thr Gly Lys Leu Pro Val Pro Trp Pro Thr Leu Val Thr Thr
        290                 295                 300

Leu Thr Tyr Gly Val Gln Cys Phe Ser Arg Tyr Pro Asp His Met Lys
305                 310                 315                 320

Gln His Asp Phe Phe Lys Ser Ala Met Pro Glu Gly Tyr Val Gln Glu
                325                 330                 335

Arg Thr Ile Phe Phe Lys Asp Asp Gly Asn Tyr Lys Thr Arg Ala Glu
            340                 345                 350

Val Lys Phe Glu Gly Asp Thr Leu Val Asn Arg Ile Glu Leu Lys Gly
        355                 360                 365

Ile Asp Phe Lys Glu Asp Gly Asn Ile Leu Gly His Lys Leu Glu Tyr
        370                 375                 380

Asn Tyr Asn Ser His Asn Val Tyr Ile Met Ala Asp Lys Gln Lys Asn
385                 390                 395                 400

Gly Ile Lys Val Asn Phe Lys Ile Arg His Asn Ile Glu Asp Gly Ser
                405                 410                 415

Val Gln Leu Ala Asp His Tyr Gln Gln Asn Thr Pro Ile Gly Asp Gly
            420                 425                 430

Pro Val Leu Leu Pro Asp Asn His Tyr Leu Ser Thr Gln Ser Ala Leu
        435                 440                 445

Ser Lys Asp Pro Asn Glu Lys Arg Asp His Met Val Leu Leu Glu Phe
        450                 455                 460

Val Thr Ala Ala Gly Ile Thr Leu Gly Met Asp Glu Leu Tyr Lys Ser
465                 470                 475                 480

Gly Leu Arg Ser Arg Ala Gln Ala Ser Asn Ser Ala Val Asp Met Pro
                485                 490                 495

Ser Asp Arg Pro Phe Lys Gln Arg Arg Ser Phe Ala Asp Arg Cys Lys
            500                 505                 510

Glu Val Gln Gln Ile Arg Asp Gln His Pro Ser Lys Ile Pro Val Ile
        515                 520                 525

Ile Glu Arg Tyr Lys Gly Glu Lys Gln Leu Pro Val Leu Asp Lys Thr
        530                 535                 540

Lys Phe Leu Val Pro Asp His Val Asn Met Ser Glu Leu Val Lys Ile
545                 550                 555                 560

Ile Arg Arg Arg Leu Gln Leu Asn Pro Thr Gln Ala Phe Phe Leu Leu
                565                 570                 575
```

```
Val Asn Gln His Ser Met Val Ser Val Ser Thr Pro Ile Ala Asp Ile
            580                 585                 590
Tyr Glu Gln Glu Lys Asp Glu Asp Gly Phe Leu Tyr Met Val Tyr Ala
            595                 600                 605
Ser Gln Glu Thr Phe Gly Phe
610                 615
```